United States Patent [19]
Athanasiou et al.

[11] Patent Number: 5,503,162
[45] Date of Patent: Apr. 2, 1996

[54] ARTHROSCOPIC CARTILAGE EVALUATOR AND METHOD FOR USING THE SAME

[75] Inventors: Kyriacos Athanasiou; George Constantinides; Dan R. Lanctot, all of San Antonio, Tex.

[73] Assignee: Board of Regents, University of Texas System, Austin, Tex.

[21] Appl. No.: 231,612

[22] Filed: Apr. 22, 1994

Related U.S. Application Data

[63] Continuation-in-part of Ser. No. 113,729, Aug. 27, 1993, Pat. No. 5,433,215, which is a continuation of Ser. No. 871,523, Apr. 21, 1992, abandoned.

[51] Int. Cl.⁶ .................................................. A61B 5/103
[52] U.S. Cl. ...................... 128/774; 364/413.02; 364/506
[58] Field of Search ...................... 128/774, 737, 128/739, 740, 744, 4, 5, 6; 73/573, 81, 82, 85, 87, 781, 855, 856, 788; 364/413.02, 505, 506, 508, 512

[56] References Cited

U.S. PATENT DOCUMENTS

| | | |
|---|---|---|
| 4,132,224 | 1/1979 | Randolph . |
| 4,159,640 | 7/1979 | Leveque et al. . |
| 4,253,467 | 3/1981 | Frazier . |
| 4,364,399 | 12/1982 | Dashefsky . |
| 4,414,962 | 11/1983 | Carson . |
| 4,461,281 | 7/1984 | Carson . |
| 4,503,865 | 3/1985 | Shishido . |
| 4,756,304 | 7/1988 | Watanabe . |
| 4,848,141 | 7/1989 | Oliver et al. . |
| 4,888,490 | 12/1989 | Bass et al. . |
| 4,896,339 | 1/1990 | Fukumoto . |
| 4,983,021 | 1/1991 | Fergason ................................. 359/36 |
| 5,003,982 | 4/1991 | Halperin . |
| 5,025,199 | 6/1991 | Ako ....................................... 318/561 |
| 5,067,346 | 11/1991 | Field . |
| 5,146,779 | 9/1992 | Sugimoto et al. . |

OTHER PUBLICATIONS

Mow, V. C. et al., "Biphasic Indentation of Articular Cartilage—II. A Numerical Algorithm and an Experimental Study," J. Biomech., (1989) 22:853–861.

Mow, V. C. et al., "Biphasic Creep and Stress Relaxation of Articular Cartilage in Compression: Theory and Experiments," J. Biom. (1980) 102:73–83.

*Primary Examiner*—Stephen C. Pellegrino
*Assistant Examiner*—Guy V. Tucker
*Attorney, Agent, or Firm*—Greenlee and Winner

[57] ABSTRACT

An arthroscopic cartilage evaluator for determining the Index of Structural Integrity of articular cartilage. This computer-based system measures deformation or reaction force of articular cartilage and processes that information for closed loop control of a testing tip and allows the measurement of stress relaxation behavior or creep behavior in vivo and in situ. This evaluator also allows the calculation of the tissue's material properties.

45 Claims, 20 Drawing Sheets

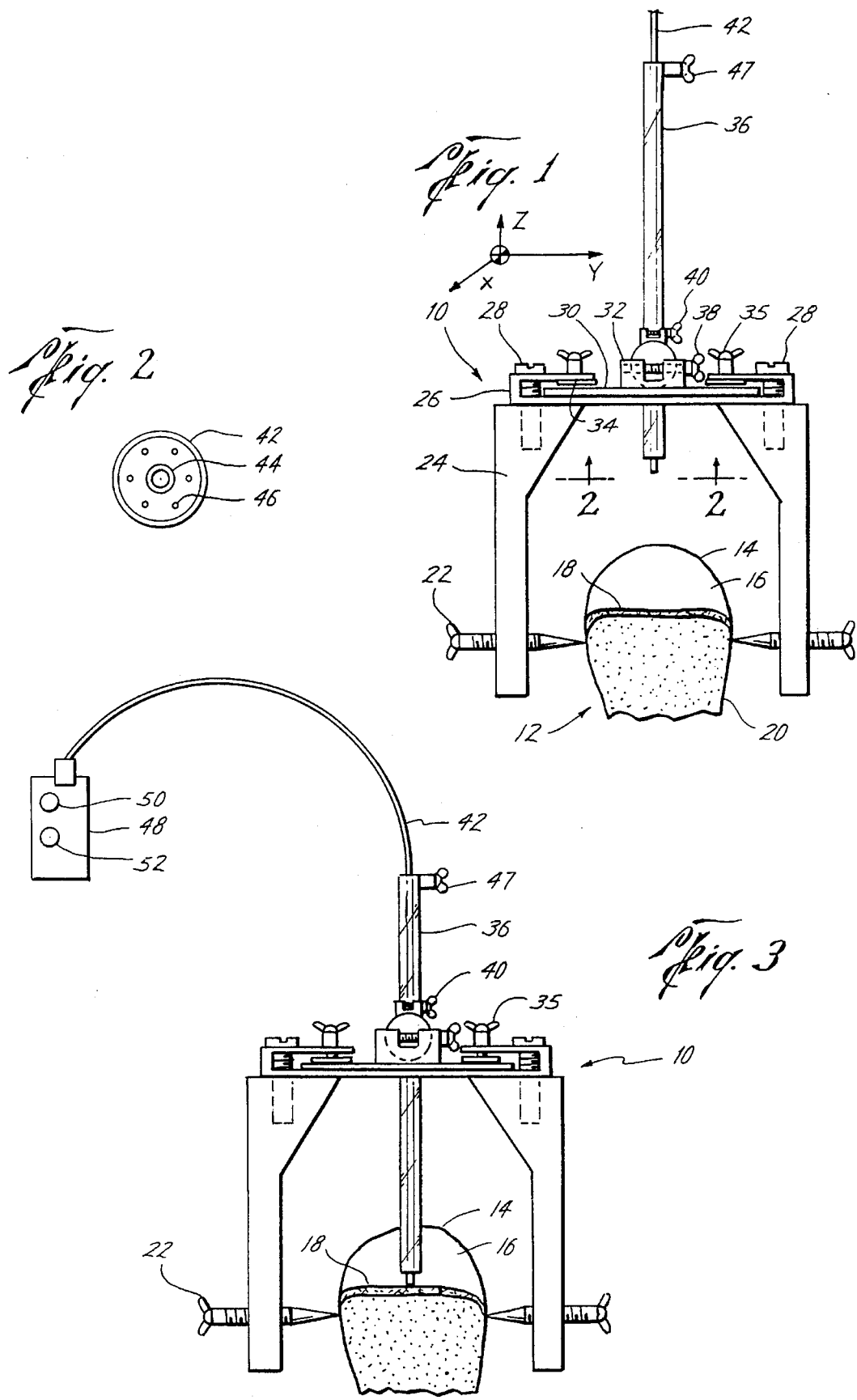

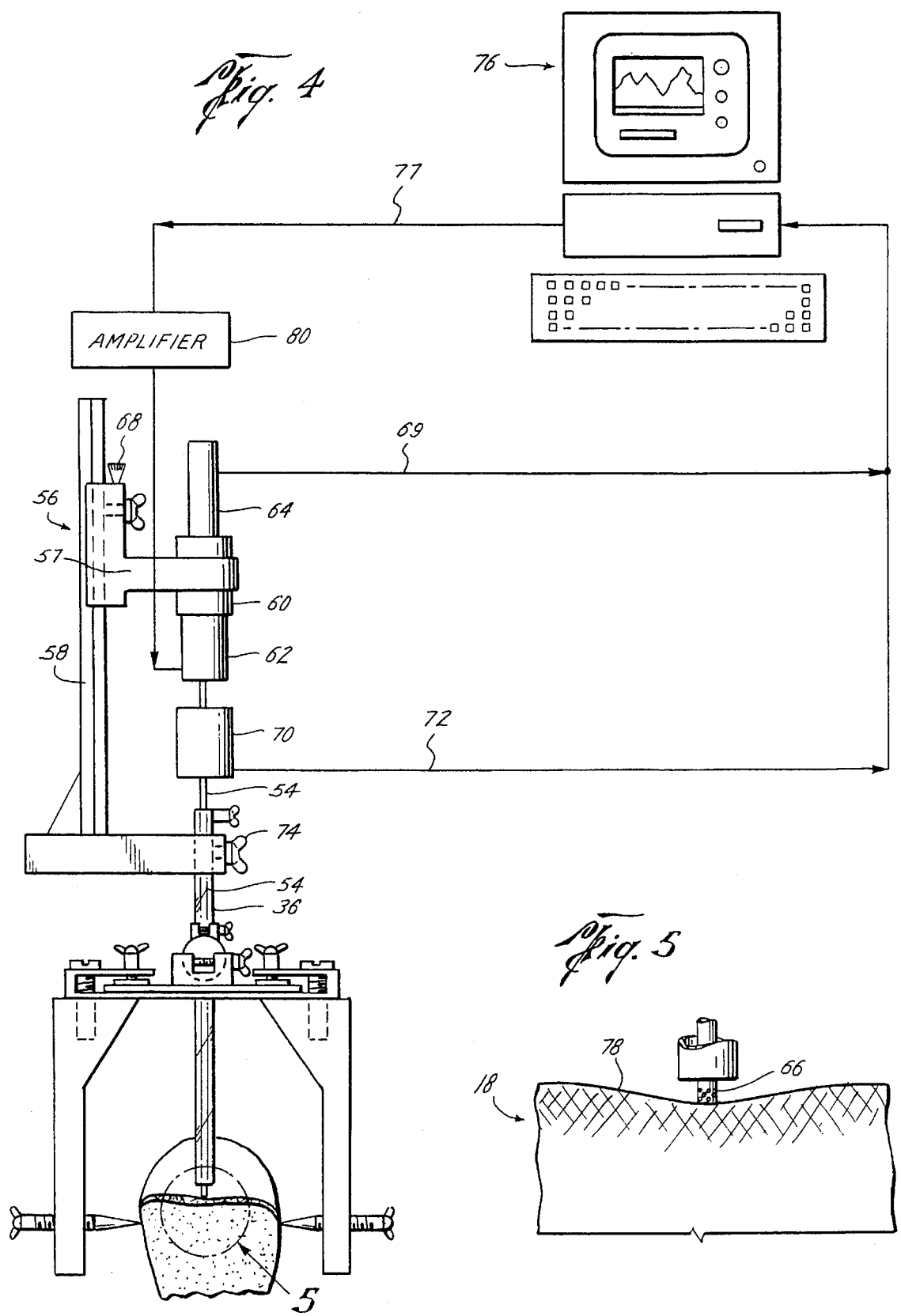

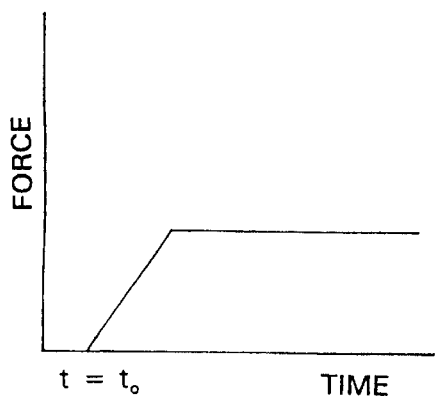
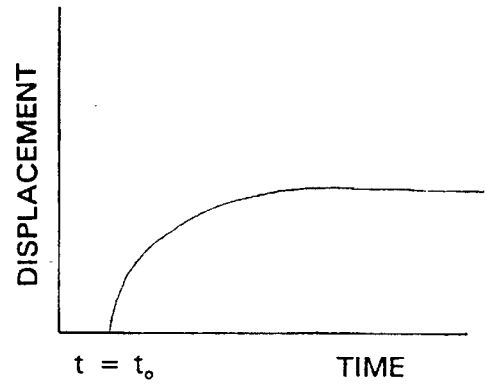
FIG. 6A FIG. 6B
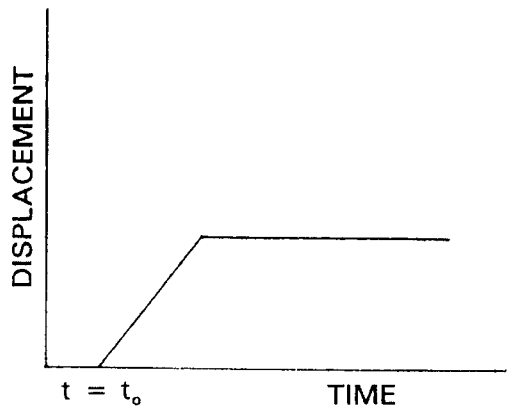
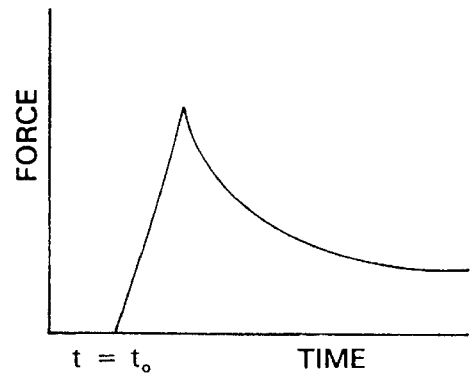
FIG. 7A FIG. 7B
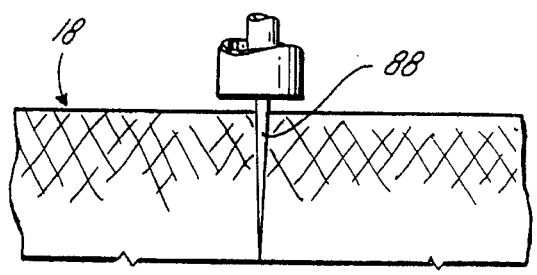
FIG. 8

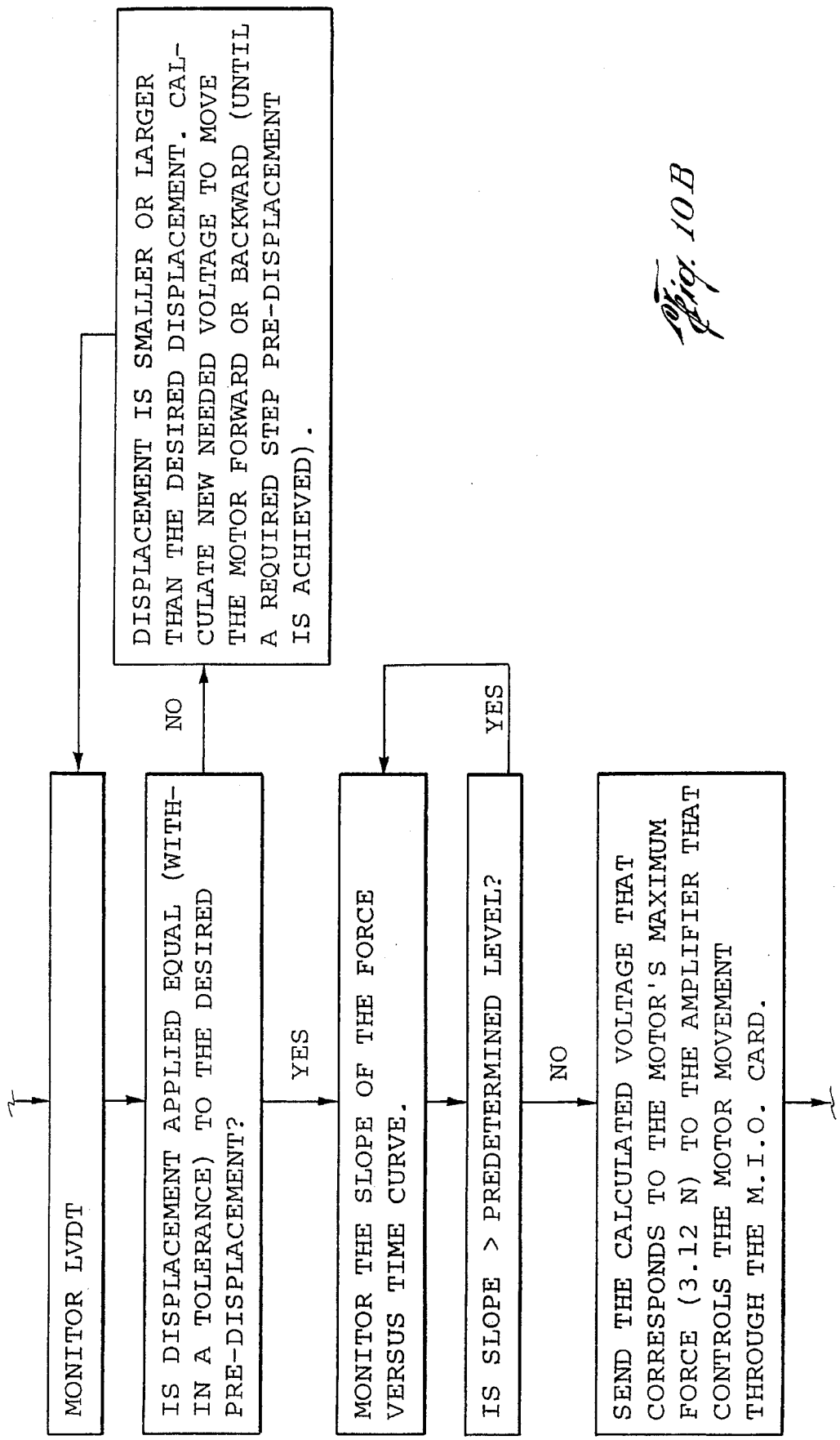

ARTHROSCOPIC CARTILAGE EVALUATOR AND METHOD FOR USING THE SAME

CROSS-REFERENCE TO RELATED APPLICATIONS

This application is a continuation-in-part of U.S. Ser. No. 08/113,729 filed Aug. 27, 1993, now U.S. Pat. No. 5,433,215, which is a continuation of U.S. Ser. No. 07/871,523 filed Apr. 1, 1992 now abandoned, said applications being incorporated herein by reference.

FIELD OF THE INVENTION

The present invention relates to an arthroscopic mechanical system in general and, more particularly, to an apparatus and method for defining and measuring the structural integrity of articular cartilage.

DESCRIPTION OF THE RELEVANT ART

The effects of articular cartilage degenerative diseases (such as osteoarthritis or chondromalacia patella) are visible to the naked eye when the disease has reached an advanced stage. Manifestations of these diseases include changes in the tissue's: 1) material properties (stiffness, permeability, compressibility), 2) biochemical composition (type II collagen, proteoglycan macromolecules, interstitial water content), and 3) morphological characteristics (surface fibrillation and fraying, osteophyte formation). At the early stages of articular cartilage degeneration, the tissue's stiffness decreases and its compressibility and permeability increase. Thus, a reliable means to quantify the initial stages of articular cartilage degeneration is to obtain its mechanical (or material) properties or characteristics. This can be accomplished during arthroscopy, which is an in vivo and in situ procedure, using a probe to examine qualitatively the articular surfaces. Using direct vision provided by an arthroscopic fiberoptic tube connected to a videocamera, the probe is used to palpate the tissue and, based on the tissue's deformation, the orthopaedist decides on the existence or severity of the disease. During this procedure, the orthopaedist also examines visually the surface characteristics of articular cartilage. This procedure is neither objective nor successful in determining the early stages of degenerative diseases, during which visual abnormalities are not present.

A device used to measure the "deformation resistance" of tissue, and particularly the articular surface of the patella, is described in U.S. Pat. No. 4,364,399. This arthroscopic instrument simply measures the amount of resistance pressure exerted by the cartilage at a given indentation. Positioning of the probe is manually accomplished, and perpendicularity of the probe relative to the cartilage surface is subjectively determined. The distance of indentation is mechanically calculated often using manual placement of the pressure transducer against the cartilage surface. A manual indentation process (as opposed to one which is computer-controlled) is not sufficiently accurate to allow repeatable, objective measurements. Manual indentation devices cannot programmably vary the applied indentations or forces in order to more accurately obtain material properties of the cartilage. This patented device does not measure the thickness of articular cartilage. Two tissues with the same material properties but unequal thicknesses will exhibit different deformation or force resistance. Thus, the thickness of the tissue must also be measured and used to normalize the measured tissue deformation or force resistance. Furthermore, the device of U.S. Pat. No. 4,364,399 is used to apply indentations onto cartilage without immobilizing the cartilage's subchondral bone relative to the device. Thus, under indentation, not only cartilage but other surrounding or underlying soft tissues deform. As a result, when both the cartilage and surrounding tissue deform, the applied cartilage indentation is not accurately known, and the measured cartilage resistance may be irrelevant. Thus, manual indentation devices provide an extremely subjective value of the tissue's deformation and force behaviors.

While indentation techniques are preferable over arthroscopic observations, manual indentation techniques which are not computer-controlled do not provide sufficient data to allow accurate and repeatable mechanical measurements to be taken of the cartilage.

SUMMARY OF THE INVENTION

The problems outlined above are in large part solved by the to apparatuses and methods of the present invention. That is, the arthroscopic evaluators hereof can, in preferred embodiments, utilize high resolution displacements or loading forces placed substantially perpendicular upon the cartilage via a testing tip. Specifically, applied or resistive forces and applied or developing displacements are measured, recorded, and fed back upon the testing tip using a closed-loop computer feedback system. The computer-controlled evaluators with feedback of this invention can more accurately and repeatably measure the material properties of articular cartilage than prior art devices using stress relaxation and/or creep deformation techniques described below.

The evaluators of this invention allow the physician to measure the material properties of cartilage and/or the Index of Structural Integrity in vive in the physician's office through small incisions, or during open joint surgery. The devices may also be used for in vitro tissue evaluation.

In one embodiment, the present invention contemplates an arthroscopic evaluator for measuring the creep deformation profile and/or the stress relaxation profile of cartilage, preferably articular cartilage. Creep deformation is the deformation of the cartilage as a function of time in response to a constant force or lead placed upon the cartilage. Stress relaxation is the resistive force exerted by the cartilage over time in response to a set displacement.

The method for measuring "creep deformation" is a method in which a constant force is applied to the cartilage surface via a testing tip and resulting cartilage displacement under the tip is measured as a function of time. The constant applied force, the ensuing displacement profile and the tissue thickness can then be used to compute material properties of the cartilage. In addition, "stress relaxation" is defined as the technique by which a constant displacement distance is applied to the tissue via the evaluator and resulting force profile is measured. The constant applied displacement, the corresponding force resistance profile and the cartilage thickness can also be used to compute the material properties of the cartilage. Either creep deformation or stress relaxation techniques can produce an accurate measure of the material properties of the cartilage such as compressive stiffness, apparent compressibility, and permeability. Stiffness, compressibility and permeability are three important factors used in predicting the location and amount of the degenerative disease existing in articular cartilage.

The arthroscopic evaluators of this invention are devices for measuring the response of cartilage, preferably articular cartilage, to indentation comprising:

(a) a loading system comprising a testing tip for placement proximate to and for indenting the cartilage during use;

(b) an alignment system adapted to align the testing tip substantially perpendicular to the cartilage during use; and (c) a system for measuring the response of the cartilage to a force applied thereto by the testing tip during use, the force being applied to displace a portion of the cartilage during use; or (d) a system for measuring the response of the cartilage to a displacement applied thereto by the testing tip during use, the displacement being applied to create a resistive force in the cartilage during use.

The loading system comprises any system known to the art for exerting force, referred to as "loading" herein, including manually-exerted force, or a computer-controlled actuator such as a motor, which moves a shaft which may be directly attached to the testing tip, or in the hand-held embodiment hereof, includes a loading force translation system for changing the direction and speed of the motion imparted by the motor shaft to the testing tip. The loading system also includes a system for controlling the amount of force exerted against the cartilage, preferably articular cartilage, by the testing tip, such as a computer-controlled feedback mechanism as described herein, or other systems known to the art.

The alignment system may comprise a reflected light system as described hereinafter, a perpendicularity rim as described with respect to the hand-held embodiment of this invention, or other systems known to the art such as non-circular flanges at the distal end of the device.

The system for measuring the response of the cartilage to the force applied may comprise any system known to the art including position detectors, force transducers, and combinations thereof, and also including computerized data collection, calculation and display components.

The apparatus includes a loading system comprising a loading shaft having a proximal end and a distal end. The distal end is a testing tip which can be placed proximate to cartilage to be measured. The term "distal" is used with respect to the operator, the "distal" end of the device being the end closest to the patient. An electromechanical actuator capable of axially moving the shaft in response to electrical input is attached to or near the proximal end of the shaft. The actuator may include a motor and a cam used to axially displace the distal end at a constant force upon the cartilage. A system is provided to measure the response of the cartilage, preferably articular cartilage, to force applied thereto. To measure creep deformation, a computer is used to programmably command the motor to apply constant force and it also records the amount by which the distal end displaces the cartilage while maintaining constant force upon the cartilage. Alternatively, to measure stress relaxation the computer commands the motor to measurably force the distal end to a set displacement upon the cartilage. The computer also records the resistive force exerted by the cartilage upon the distal end at the set displacement distance.

This embodiment further comprises a system for aligning the loading shaft. The system includes a frame positioned proximate to the cartilage and a protective sheath attached to the frame which is a tube in which the loading shaft is disposed. The protective sheath includes a positioning shaft having a distal tip which can be securably positioned substantially perpendicular to the surface of the cartilage. The loading shaft may then be slidably placed within the sheath, whereby the distal end of the loading shaft is then placed in substantially perpendicular contact with the cartilage.

This embodiment also contemplates an apparatus for closed-loop controlling creep deformation and stress relaxation tests performed on cartilage. The apparatus includes a loading system having a proximal end and a distal end, wherein a testing tip at the distal end is placed substantially perpendicular to or near cartilage to be measured. A motor may be attached to the proximal end to extend the distal end upon the cartilage, and a computer is adapted to monitor force and displacement readings of said cartilage by actuating the motor a set distance or a set force in accordance with closed-loop input sent from the proximal end to the computer.

According to one aspect of the apparatus for closed-loop controlling creep deformation and stress relaxation, a force transducer is attached to or included within the loading system to measure force applied to the cartilage by the testing tip or the resistive force applied by cartilage against the testing tip. A position detector is also coupled to the loading system to measure the distance by which the testing tip extends upon the cartilage. The computer operates on a closed loop principle by receiving input from the force transducer and position detector, and then outputting programmed electrical signals to the motor in accordance with the input.

The present invention also contemplates methods and systems for determining substantially perpendicular placement of an arthroscopically placed loading shaft upon the outer surface of the cartilage. One method includes fixing a frame proximate to an articular joint and movably securing a protective sheath to the frame. A light transmitter and at least three light receivers can be slidably placed into the protective sheath to direct a light beam at the surface of the cartilage and then detect light reflected from the surface. The protective sheath is then secured to the frame when the detected light received upon the receivers is at a maximum, thus indicating perpendicularity. In a further embodiment hereinafter described, means for assuring perpendicular placement of the device for measuring cartilage properties comprises a perpendicularity rim at the distal end of the device.

The present invention also contemplates a method for determining material properties of cartilage, preferably articular cartilage. The method includes positioning the testing tip at the distal end of the device through skin substantially perpendicular to underlying cartilage. The distal end is then measurably extended upon said cartilage at a measurable force, wherein material properties can be calculated from measuring the force and the distance by which the testing tip extends into the cartilage.

The invention also comprises a computer adapted to calculate the Index of Structural Integrity (ISI) of the cartilage, preferably articular cartilage, as an indication of the health of the cartilage.

A further embodiment of the invention provides a hand-held device wherein the testing component may be hand-held by the physician during use to measure the salient material properties of cartilage, preferably articular cartilage, in situ and in vivo. This embodiment, termed the "Arthroscopic Cartilage Evaluator" or "ACE" herein, is a miniaturized version of the above-described embodiment preferably comprising a handle between about 5 mm and about 20 mm in diameter, and a head for insertion through the skin between about 2 mm and about 10 mm in diameter, with a testing tip having a diameter of less than about 2 mm, preferably about 0.5 mm.

The device may be used to measure stress relaxation of articular cartilage, maximum force required to displace the cartilage a predetermined distance, and force required to maintain said displacement after the cartilage has reached equilibrium. These measurements are performed within ten seconds or less, preferably within about 3 seconds or less. In a preferred embodiment, measured data are used to compute and express, preferably by means of display, a value indicating the relative health of the tissue. Preferably this value is a ratio termed herein the "Index of Structural Integrity" or "ISI." This index is a number from one to ten wherein ten represents healthy tissue and one represents severely degenerated tissue. The value is derived from measured properties of the cartilage compared to a database comprising values for cartilage having known states of health. Preferably the database comprises mean values for the measured properties of healthy tissue of the same type as that being evaluated. "Tissue of the same type" means tissue taken from the same location in the body, e.g. when tissue from the central portion of the anterior aspect of the medial femoral condyle is being evaluated, it is compared with corresponding measurements for healthy tissue from the central, anterior medial femoral condyle in the database, preferably with mean measurements for several, e.g. at least about twelve of such measurements for healthy tissue. Preferably the measurement for healthy tissue is assigned a value of ten and the ratio is expressed as an integer from one to ten (the ISI).

Like the embodiment described above, a preferred embodiment of the ACE comprises a loading system terminating in a testing tip for placement proximate to, and for indenting the cartilage during use. The ACE consists of a hand-held component comprising a handle portion and a shorter portion or head at an angle thereto between about 30° and about 180°, preferably about 90°. The handle portion contains a motor operatively connected to a motor shaft whereby the motor produces horizontal (axial) motion in the motor shaft during use. The head is inserted through the patient's skin to contact the cartilage to be tested and comprises a force translation system for changing the direction and speed of motion imparted by the motor shaft, said force translation system comprising a slider attached to the distal end of the motor shaft engaged within a slide disposed within the head at an angle such that when the slider moves forward on the slide, the slide pushes down against a loading wedge beneath it, which in turn pushes down against a force transducer, the probe at the distal end of which pushes against the testing tip of the device. The testing tip at the distal end of the head is used to indent the cartilage. Preferably, the amount of horizontal motion by the motor shaft is translated to a lesser amount of motion of the testing tip. The loading system, comprising the foregoing components involved in exerting and translating force from the motor to the testing tip, thus causes the testing tip which is placed distal to the loading wedge, to move against and displace a portion of the cartilage tissue.

The hand-held portion of the device also comprises a position detector to measure the distance travelled by the motor shaft or the testing tip, preferably the motor shaft, in response to actuation by the motor. Preferably the position detector comprises an optical encoder having a displacement resolution of about 0.1 μm.

The force transducer is adapted to provide data to determine the force applied by the testing tip to the cartilage over time. The force transducer is preferably placed between the loading wedge and the testing tip and comprises a surface placed in pressure communication with the loading wedge. Examples of force transducers include strain gauge based transducers and piezo electric transducers.

The hand-held portion of the ACE is connected to a computer programmed to measure and control the movement of the testing tip over time in response to data from the force transducer or position detector or both.

The distal end of the hand-held component of the ACE comprises an alignment system for aligning the testing tip substantially perpendicular to an outer surface of the cartilage during use. The outer sheath of the head of this component may be equipped with a perpendicularity rim for placing adjacent to the surface of the cartilage during use which serves as an alignment system for the testing tip. Alternatively, the distal end of the sheath is adapted to receive a replaceable tip assembly which includes a perpendicularity rim for placing against the surface of the cartilage.

The ACE is adapted to measure stress relaxation and creep deformation. These data can then be used to calculate the material properties of articular cartilage or the Index of Structural Integrity (ISI). Because of the small size of the ACE and the extremely small depth of indentation required compared to cartilage thickness at the test site, the thickness of the cartilage need not be measured in order to calculate the material properties and/or the ISI. The ACE also may be used to display the Index of Structural Integrity as an aid to orthopaedic diagnosis of the cartilage.

Methods for determining the response of cartilage, preferably articular cartilage, to indentation are also provided herein comprising positioning a testing tip through skin substantially perpendicular to underlying cartilage, displacing a portion of the cartilage with the testing tip; and measuring the response of the cartilage. The response of the cartilage may be measured in terms of force exerted against the testing tip by the cartilage at a set displacement or displacement of the cartilage at a constant applied force applied by the testing tip. Preferably these measurements are compiled over time by a computer system and may be used to control the force exerted by the testing tip against the cartilage during the test and to calculate the properties of the cartilage.

BRIEF DESCRIPTION OF DRAWINGS

Other objects and advantages of the invention will become apparent upon reading the following detailed description and upon reference to the accompanying drawings in which:

FIG. 1 is a perspective view of an alignment system for aligning a loading shaft according to the present invention;

FIG. 2 is a cross-sectional view along plane 2—2 of FIG. 1;

FIG. 3 is a perspective view of the alignment system utilizing a fiber optic alignment arrangement according to the present invention;

FIG. 4 is a perspective view of an apparatus for determining material properties of articular cartilage according to the present invention;

FIG. 5 is a detail view of section 5 of FIG. 4;

FIGS. 6A and 6B are graphs showing creep deformation at constant force achievable by the present invention;

FIGS. 7A and 7B are graphs showing stress relaxation at constant displacement achievable by the present invention;

FIG. 8 is a detail view showing a needle thickness probe placed at the distal end of the loading shaft;

Figure 9A:
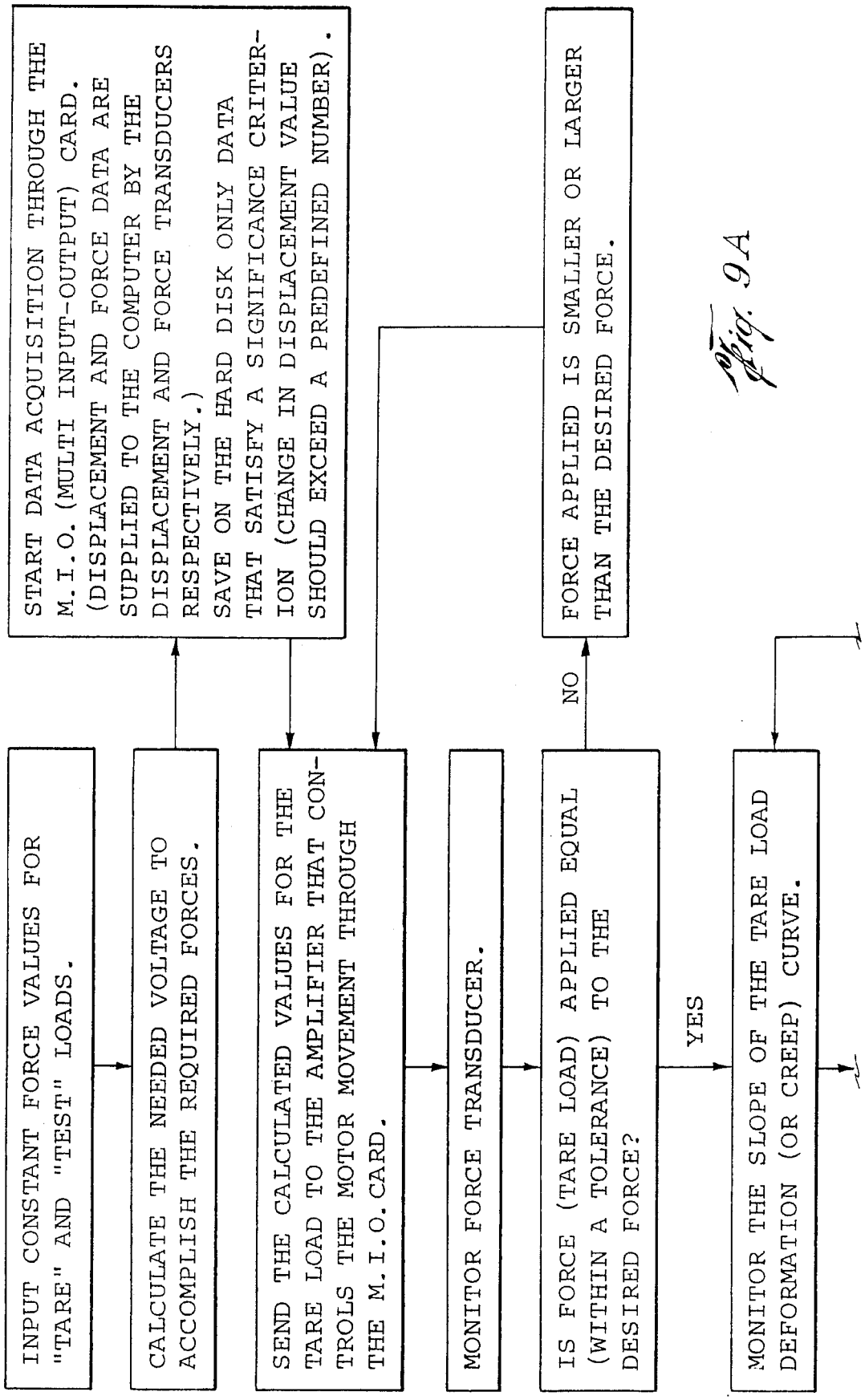
FIGS. 9a and 9b present a flow diagram of steps used to perform creep deformation achievable by the present invention.

While the invention is susceptible to various modifications and alternative forms, the specific embodiments thereof have been shown by way of example in the drawings and will herein be described in detail. It should be understood, however, that the drawings are not intended to limit the invention to the particular form disclosed, but on the contrary, the intention is to cover all modifications, equivalents and alternatives falling within the spirit and scope of the invention as defined by the appended claims.

DETAILED DESCRIPTION OF THE INVENTION

Turning now to the drawings, FIG. 1 illustrates an alignment system 10 affixed to, for example, diarthrodial joint 12. Joint 12 includes skin 14 over a soft tissue 16, articular cartilage 18 and bone 20. Without limiting the scope of the present invention, articular cartilage 18 as well as other forms of hard or soft tissue may be mechanically characterized by the present invention.

Alignment system 10 is mounted on joint 12 using at least two thumb screws 22 as shown in FIG. 1. Screws 22 preferably extend through skin 14 and rigidly attach to bone 20 at tile distal tip of each screw 22. Bone 20 provides a rigid foundation upon which frame 24 can be securably fixed. Thus, during use, frame 24, screw 22 and bone 20 remain in fixed relationship to each other.

Housing 26 is fixed at one end of frame 24 by a suitable machine bolt 28 placed through housing 26 and into frame 24. Confined between bolts 28 and within housing 26 is a moveable plate 30. Plate 30 has two opposing planar surfaces upon which a ball socket clamp set 32 is affixed substantially near the center of one plane. Plate 30 and attached clamp set 32 are moveable in two dimensions (i.e., along the x and y axes) by removing the tension between the pad 34 and plate 30. Once the desired x and y position is determined, thumb screws 35 are tightened causing plate 30 to be drawn tightly between housing 26 and pads 34.

Clamp set 32 as well as plate 30 and housing 26 all have an opening or port through which a protective sheath 36 can be placed. Clamp set 32 with ball-and-socket reciprocation allows sheath 36 to be tilted in a variety of angles with respect to frame 24. Once a desired angular tilt is established, a first locking thumb screw 38 can be tightened, thus fixing sheath 36 at the desired angular position. Moreover, sheath 36 can be moved along an axis substantially perpendicular to the plane formed by the x and y axes (i.e., along the z axis) by displacing sheath 36 within the passage formed through clamp set 32, plate 30 and housing 26. Once the proper z displacement is achieved, second locking thumb screw 40 can be tightened thereby affixing sheath 36 to clamp set 32.

Sheath 36 is tubular in shape and can be of varying geometry. A suitable geometry is a length of approximately 15 cm with a 4.6 mm outside diameter. Sheath 36 is made of any form of rigid material including but not limited to surgical quality stainless steel, titanium-base alloys, or cobalt-base alloys. A nominal inside diameter of sheath 36 may be approximately 4.2 mm to accommodate an alignment shaft 42.

As shown in FIG. 2, alignment shaft 42 is a cylindrical body that encapsulates a fiber optic cable 44 through which a light from a light source can pass. At least about three receivers 46 can be arranged at a radially spaced distance from cable 44. Receiver 46 may include either a fiber optic cable arranged substantially parallel to cable 44 for receiving reflected light or a photodiode arranged at the distal tip of shaft 42 for converting reflected light to electrical signal.

As shown in FIG. 3, the distal tip of alignment shaft 42 can be placed proximate to the outer surface of articular cartilage 18 but spaced a small distance therefrom. The distal end of alignment shaft 42 is inserted through an incision of approximately 5 mm length formed in skin 14. A 5 mm incision is a typical incision geometry used in normal arthroscopy. The distal end follows the insertion down to the point of interest proximate to articular cartilage 18. Alignment shaft 42 is then locked in place relative to sheath 36 with a thumb screw 47. It is of primary importance that alignment system 10 be used to align protective sheath 36 in a substantially perpendicular orientation to articular cartilage 18 residing directly beneath sheath 36. Accordingly, alignment shaft 42, carrying fiber optic cable 44 and one or more receivers 46, is used to align sheath 36 in a substantially perpendicular orientation. Namely, alignment is achieved by transmitting light waves through fiber optic cable 44 to illuminate a circular area upon articular cartilage 18. The area is approximately 1.0 mm in diameter and indicates the transmitted light waves striking articular cartilage 18 and reflecting therefrom. The reflected waves are detected as they strike receivers 46 placed radially around cable 44. Alignment shaft 42 is tilted via clamp set 32 and/or translated in the x or y axes via moveable plate 30 until the transmitted light waves reflect directly back onto receivers 46 from a substantially perpendicularly arranged portion of the surface of articular cartilage 18. This occurs when receivers 46 sense maximum detected quantity of light waves. Instead of only one or two radially spaced receivers detecting light (indicating a tilt condition), all detectors receive a maximum amount of light of somewhat equal magnitude. When receivers 46 receive maximum reflected light, indicator 48 produces a visual light 50 or an audible alarm 52, or can be read by the computer.

Receivers 46 may be either fiber optic cables for receiving reflected light or photodiodes (preferably PIN photodiodes) for converting reflected light to electrical signals which are then transmitted through shaft 42 to indicator 48. Either form of detector may be used. A suitable alignment shaft including fiber optic cable 44, receivers 46 and indicator 48 is produced by Keyence Corp. of America, Fair Lawn, N.J. as Model No. FS2-60.

Once protective sheath 36 is securably positioned substantially perpendicular to a portion of the surface of articular cartilage 18 directly beneath sheath 36, alignment shaft 42 can be removed from the sheath 36. An appreciable advantage of the present invention is the various degrees of movement and rotation which can be adjustably applied upon sheath 36. Once the desired position is detected, convenient thumb screws 35, 38, 40 can be tightened to fix the relative position of sheath 36 in relation to articular cartilage 18. Sheath 36 thereby provides a positioning passageway into which loading shaft 54 can be placed as shown in FIG. 4. Coupled to one end of loading shaft 54 is a servo motor assembly 62. Unislide assembly 57 functions to allow coupler 60 and attached hardware to slide upon servo motor assembly 56. Coupler 60 is used for attaching an electromechanical actuator or motor 62, with an axially moveable shaft, to positional detector 64.

Loading shaft 54 is preferably made of stainless steel with approximately 2.0 mm outside diameter with a sintered steel porous testing tip 66 placed at the distal end of loading shaft 54. Housing 58 and the base of servo motor assembly 56 are made of any form of rigid material such as, for example, stainless steel or aluminum. A suitable servo motor may be obtained from Northern Magnetics, Inc. Model No. ML2-1005-007JBT having a stroke of 12.7 mm and a maximum continuous force of 3.12 N and continuous power of 4.5 Watts. A suitable servo motor assembly 56 may be obtained from Velmex, Inc. Model No. A1503K2-S1.5 with a maximum unislide travel distance of 38.1 mm and having lead screw 68 with transverse movement of 1 cm per 5 turns. Still further, a suitable positional detector 64 is a linear variable differential transformer (LVDT) manufactured by Trans-Tek, Inc. Model No. 0242-0000 A-91 having a range of approximately ± 6.35 mm with an excitation voltage of 6 volts DC to 30 volts DC. Positional detector 64 produces an analog output 69 signifying the relative position of loading shaft 54. The analog output 69 is of substantially infinite resolution.

Also attached between motor 62 and shaft 54, at the proximal end of shaft 54, is a force transducer 70 adapted to measure the amount of force applied to articular cartilage 18 by loading shaft 54, which is the same as the resistive force applied to shaft 54 by internal mechanical resilience of articular cartilage 18. Force transducer 70 may be obtained from Transducer Techniques, Inc. Model No. MDB-5 having a range of −22.3N (compression) to +22.3N (tension). Excitation voltage upon Model No. MDB-5 is approximately 10 volts DC having an electrical analog output 72, which is substantially infinite in resolution.

Loading shaft 54 is inserted into sheath 36 which in turn is locked into place with sheath lock 74, and unislide housing 58 and the outer housing of positional detector 64 are rigidly attached to each other. Shaft of motor 62, force transducer 70, inside moveable core of positional detector 64 and loading shaft 54 (with testing tip 66) are fixed in position relative to each other and move as a unit. As a result, the unislide lead screw 68 controls the position of testing tip 66 relative to articular cartilage surface 18. Testing tip 66 is translated with unislide lead screw 68 to close proximity to the surface of articular cartilage 18. Testing tip 66 will then be used in both creep deformation testing and stress relaxation testing to determine the material properties of articular cartilage 18.

Creep deformation testing begins by utilizing a computer 76 with feedback closed-loop control, which sends an analog signal 77 via amplifier 80 to motor 62. By way of example, computer 76 receives programmed input to apply a load force (e.g., 0.0687N tare load) via a 2.0 mm diameter flat-ended cylindrical, rigid, porous testing tip 66. The loading tare force is delivered by output signal 77 sent from computer 76 to motor 62 through amplifier 80. The tare force remains constant and is used to allow the operator to establish a reliable starting level (or zero position) of the tissue's surface. As the articular cartilage surface 18 deforms, the positional detector 64 core moves relative to the outer housing of detector 64 and produces an analog signal 69 (voltage) which is linearly related to the amount of displacement recorded by detector 64. The slope of the graph of deformation versus time for this tare load creep is monitored by the computer and when the slope becomes smaller than a pre-programmed amount (e.g., $1 \times 10^{-6}$ mm/s) computer 76 sends a new signal output 77 through amplifier 80 to motor 62. Motor 62 then responds by increasing the force upon articular cartilage 18 via testing tip 66. The increased load (e.g. 0.438 N) is used to further deform articular cartilage 18 caused by axial movement of testing tip 66.

Creep deformation is the deformation of articular cartilage 18 as a function of time in response to a constant force or load placed upon articular cartilage 18. Positional detector 64 output is collected by computer 76 via multi-input/output card (not shown) (National Instruments, Model No. NB-MIO-16XL-42) within computer 76. Multi-input/output card receives analog input 69 from detector 64. Data points are then collected and plotted on the screen every 2.5 μm of deformation-change or every 100 seconds, whichever happens first, for ten minutes. At the end of ten minutes, the test load is removed and articular cartilage 18 is allowed to recover for approximately 8 minutes at which time data acquisition ceases automatically as determined by program input within computer 76.

FIG. 6A is a graph illustrating the constant force applied by the indention tip. FIG. 6B shows a typical, corresponding, articular cartilage deformation profile as a function of time. Creep deformation is particularly suited for measuring the material properties, e.g. compressibility, stiffness and permeability, or the ISI of articular cartilage 18.

Similar to the creep deformation equilibrium measurement technique described above, stress relaxation equilibrium measurement utilizes the same apparatus while applying a different programmed technique. Instead of applying a constant force and measuring the resulting displacement, the stress relaxation technique applies a set displacement upon testing tip 66 and measures the resulting resistive force exerted by articular cartilage 18 upon testing tip 66 as shown in FIGS. 7A and 7B. The stress relaxation technique utilizes an initial displacement of, e.g., 10 μm applied substantially perpendicular to articular cartilage 18 by motor 62 to begin data acquisition of resistive force. The slope of the graph of this resistive force versus time is calculated and when it becomes sufficiently small (e.g., $1 \times 10^{-6}$ N/s), computer 76 sends new output voltage 77 through amplifier 80 to motor 62 which corresponds to the maximum force of approximately 3.12 N to achieve a constant cartilage displacement (step displacement) of, e.g., 0.2 mm under testing tip 66. Positional detector output 69 is monitored until the desired step displacement of, e.g., 0.2 mm is achieved, while force transducer 70 measures the reaction or resistive force developed by articular cartilage 18 as a response to the applied step displacement. This resistive force is expected to increase very fast as a function of time to the applied step displacement as shown in FIGS. 7A and 7B. Thereafter, resistive force will decrease or "relax" to an equilibrium point as shown in FIG. 7B.

Stress relaxation, creep deformation, and thickness provide inputs by which material properties of articular cartilage 18 can be obtained. Such properties include, but are not limited to, compressive stiffness, apparent compressibility and permeability. Permeability is the degree of difficulty of movement of articular cartilage 18 interstitial fluid in and out of extracellular solid matrix or collagen material. Thus, arthroscopic evaluator 10 can be used as either a prognostic or diagnostic tool in orthopaedics by obtaining variations in material properties of articular cartilage in a joint. An orthopaedic physician can thereby use the present apparatus to identify areas with potential for degeneration. This information will help the physician suggest changes in physical activities and exercise, and design surgical strategies which can alleviate mechanical stresses in these subject areas. Thus, the process of degenerative disease may be curbed.

An additional variable used in obtaining material properties using the device hereof includes measurement of articular cartilage thickness at the test site. Testing tip 66 can be replaced with a needle thickness probe 88 having a substantially smaller outside diameter than, for example, the 2.0 mm diameter testing tip 66. An exemplary needle 88 is illustrated in FIG. 8 having a nominal diameter of approximately 0.1 mm.

To measure thickness of articular cartilage 18, motor 62 is instructed by computer 76 to move needle 88 until needle 88 encounters a larger resistive force provided through contact with articular cartilage. The needle translates through articular cartilage until a sudden increase in resistive force, e.g., 3 N, indicates the needle's contact with underlying denser material such as bone. As needle 88 moves, its position is monitored with positional detector 64. Thus, at each instant both the resistive force of needle 88 and its position are simultaneously recorded by computer 76 until resistive or resultant force reaches 3 N. When needle 88 travels through air, it encounters no appreciable resistance and the force is 0 N. When the needle comes into contact with articular cartilage 18, a force gradient is registered by force transducer 70. When needle 88 encounters the calcified portion of articular cartilage 18 lying within the deep zone of the articular cartilage or when needle 88 encounters bone 20, force transducer 70 signifies that it has traveled through the entire measurable articular cartilage layer. A second force gradient is observed by force transducer 70 which signifies this increase in resistive force.

Computer 76 operates as a processor which receives analog input 69 and 72, stores and/or processes that analog input, and sends a corresponding resultant output 77. Software may be programmed within computer 76 (e.g., a Macintosh IIcx, Apple Computer Inc., having 8 MB RAM) using an object-oriented programming language (e.g., Labview, National Instruments, Inc.). Analog output 77 from computer 76 can be amplified using amplifier 80. A suitable amplifier 80 may be obtained from Aeroteck, Inc. Model No. 3010-LS. Amplifier 80 can produce a continuous output current of up to approximately 3 amperes having a continuous power dissipation of 70 watts. A reproducible gain of 1.2 amps/volt is achievable over a bandwidth of 500 Hz using Model No. 3010-LS. Output from amplifier 80 is supplied to servo motor 62 as specified hereinabove.

Any algorithm which utilizes stress relaxation and creep deformation data obtained hereinabove and then applies that data to obtain material properties, such as compressibility, stiffness and permeability, falls within the scope and spirit of this invention.

Figure 9B:
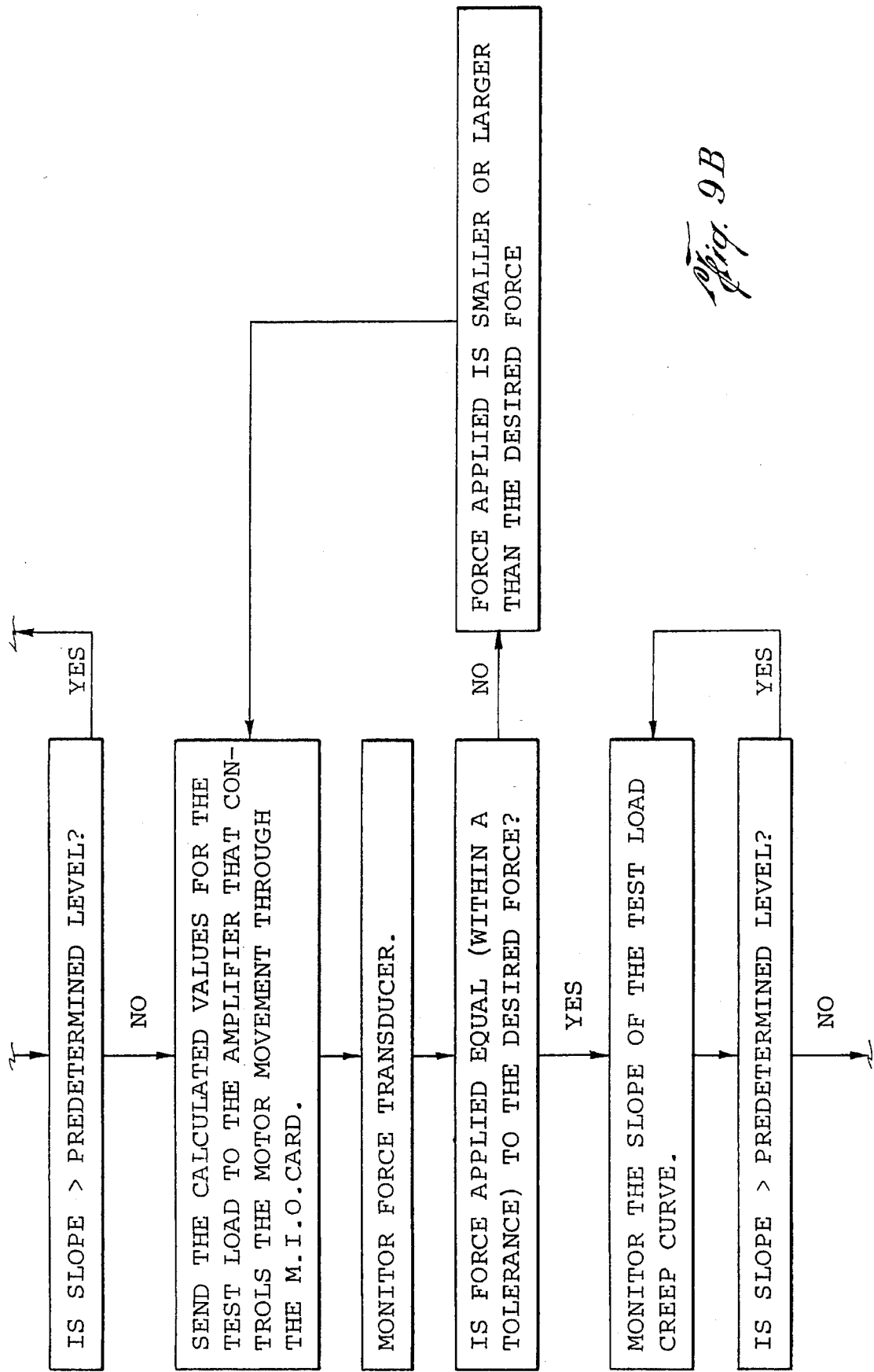
Figure 9C:
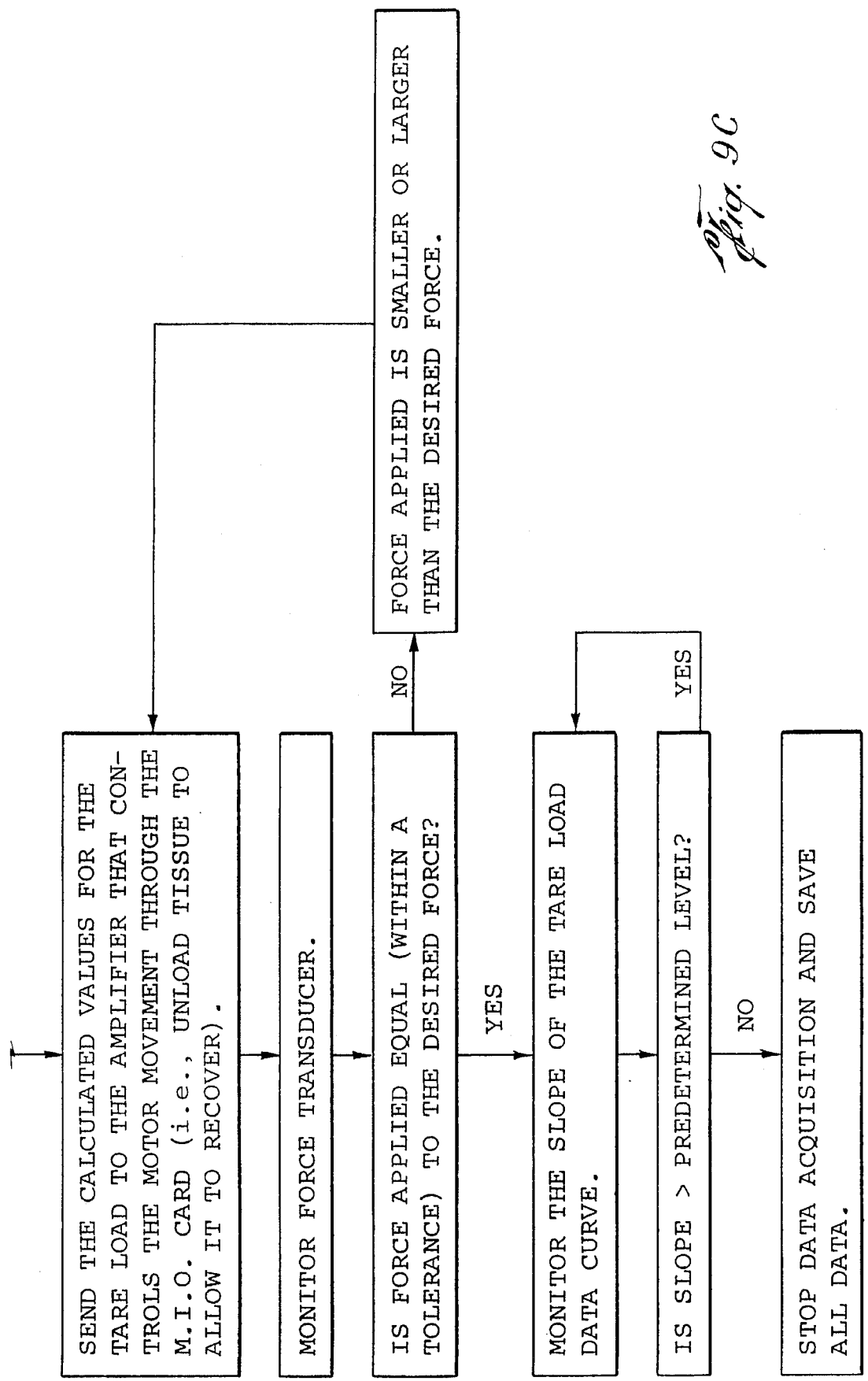
Figure 10A:
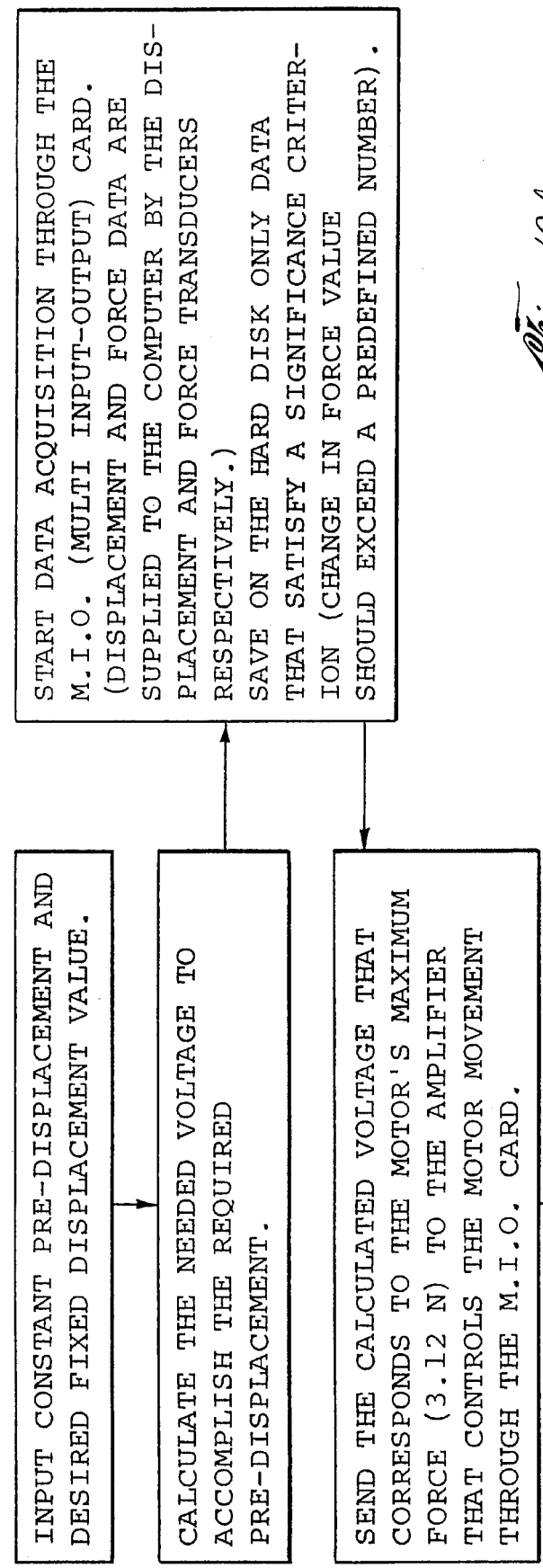
FIGS. 10a and 10b present a flow diagram of steps used to perform stress relaxation achievable by the present invention.
Figure 10C:
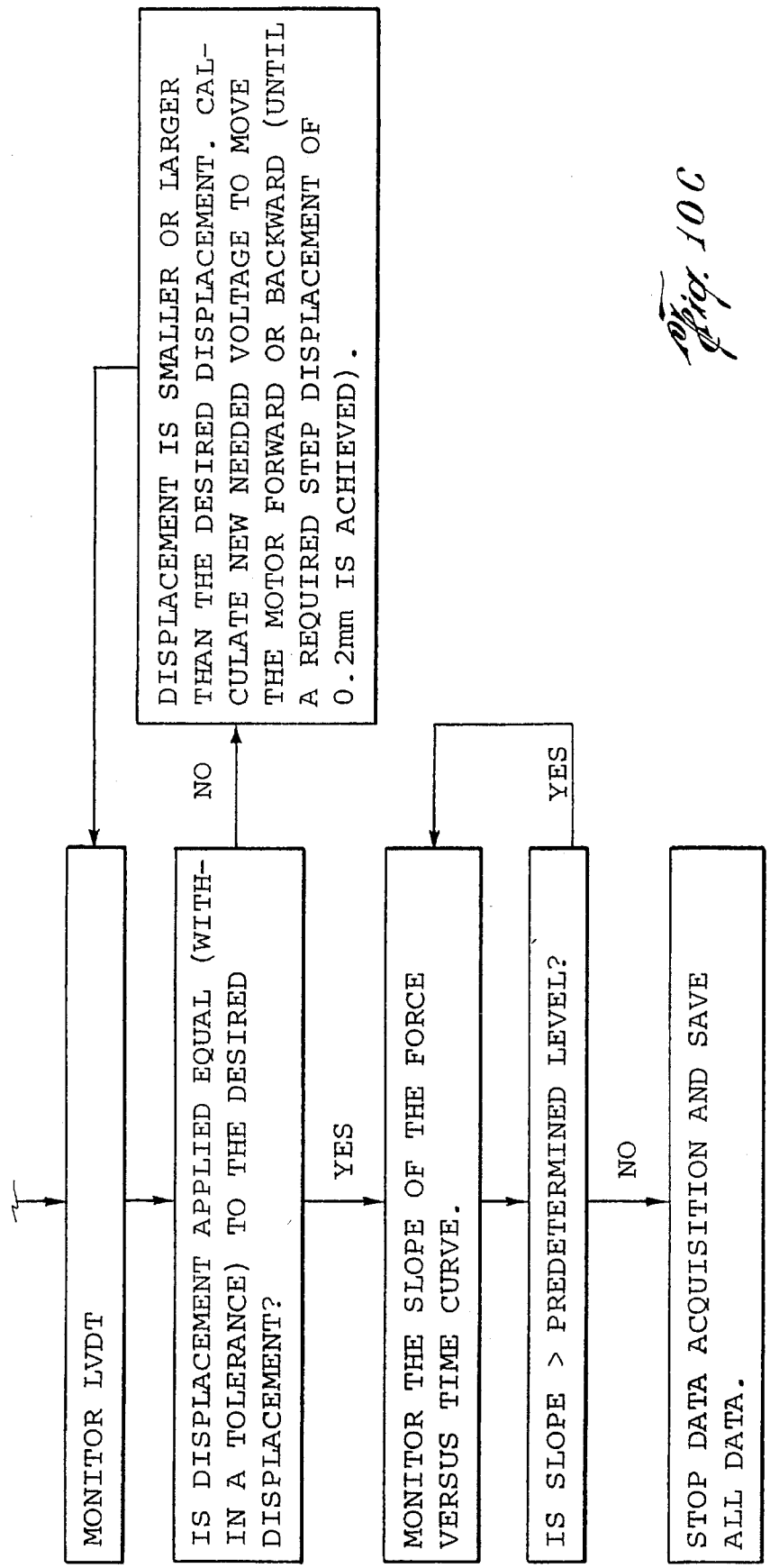
Figure 11:
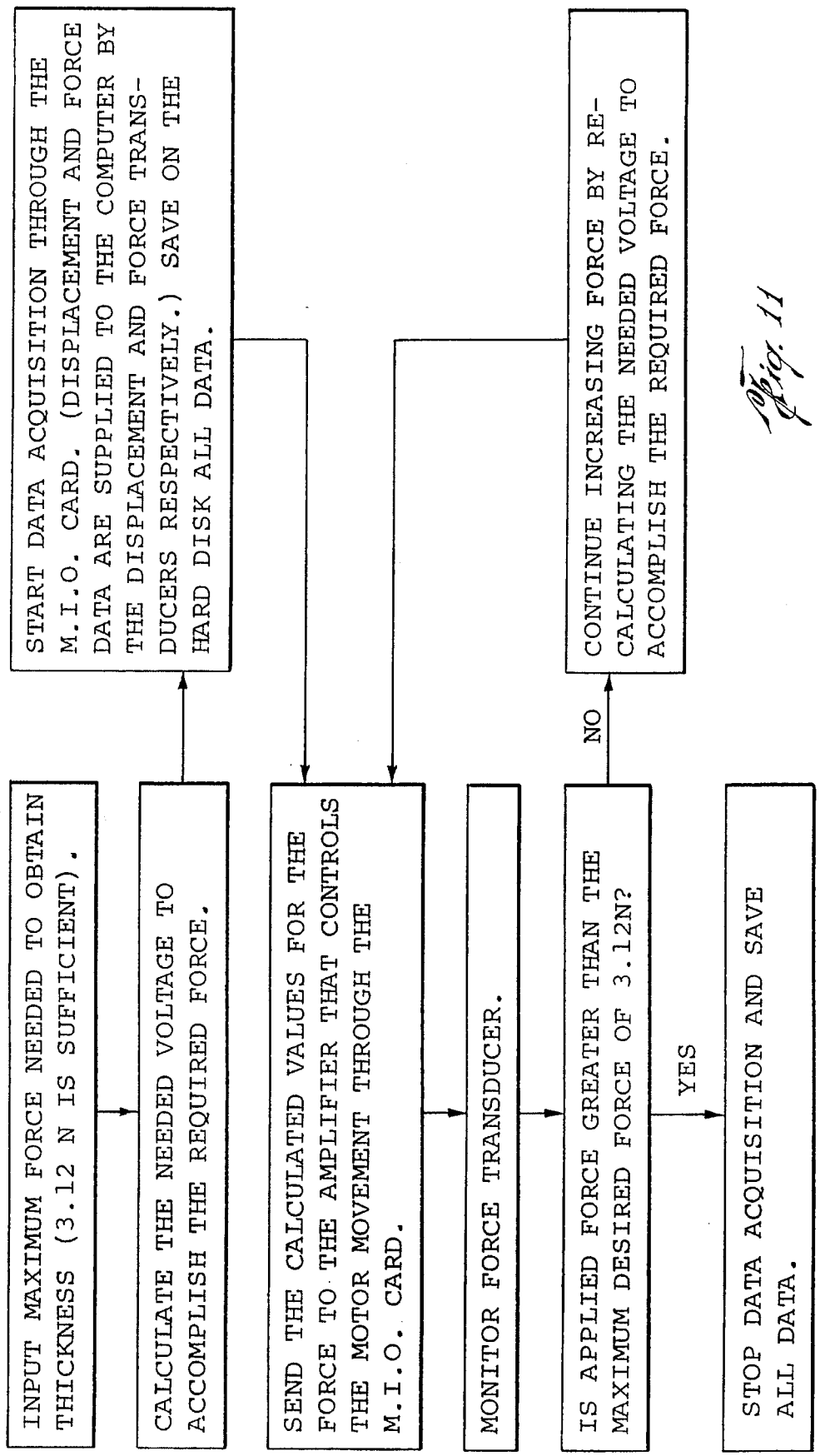
FIG. 11 is a flow diagram of steps used to perform thickness test achievable by the present invention.

Flow diagrams of various programming steps, capable of being input into computer 76, and necessary to achieve creep deformation, stress relaxation and thickness measurements are illustrated in FIGS. 9–11. Any suitable program language operable with computer 76 can be utilized to reconfigure the computer to achieve the necessary test steps.

As shown in FIG. 9, creep deformation includes numerous programmable steps beginning with both tare and test loads being input into computer 76. The tare and test loads are constant force values which computer 76 will use to monitor deformational characteristics of articular cartilage 18. A multi-input/output (MIO) card associated with computer 76 controls and monitors both the tare and test loads and displacement applied to the testing tip 66 of the present invention. The tare load is calculated in terms of voltage and sent to amplifier 80 which then controls movement of motor 62. The resulting force is monitored by force transducer 70. If the applied tare load is substantially equal to the desired force or load, then the slope of the tare load deformation or tare creep curve is monitored. If the slope of the tare creep curve is less than a predetermined level, then test operations can begin.

Creep deformation testing begins after tare loads are applied. Specifically, testing begins by sending calculated values for the test load to amplifier 80 which then controls motor 62. As stated above, tare load is generally less than test load and is used to initialize or set a bench mark for subsequent test readings. After the test load is applied via motor 62, force transducer 70 will monitor the resulting force to determine if the force applied, or test load, is substantially equal to the desired force. If test load is substantially equal to desired force, then the slope of the test load creep curve is monitored to determine if the slope is less than a predetermined level. Once the slope drops below the predetermined level, data acquisition and control stops and the experiment is finished.

Throughout the creep deformation process, a closed-loop system allows close monitoring of resultant force upon transducer 70 and readjustment of applied force sent by motor 62. The closed-loop system is controlled by programmed reconfiguration of computer 76. The software program necessary to achieve reconfiguration resides on hard disk of computer 76 or it can be stored on a portable memory medium such as a floppy disk, CD ROM, etc.

FIG. 10 illustrates the programmable steps used in achieving stress relaxation measurements by the system of the present invention. Similar to creep deformation, stress relaxation can measure the behavior of articular cartilage 18 in response to various displacement values exerted upon the articular cartilage. However, unlike the constant force values used in creep deformation, stress relaxation uses constant or fixed displacement values. In particular, stress relaxation requires a fixed displacement value be sent from computer 76 to motor 62. The desired voltage needed to accomplish the required pre-displacement is calculated and also sent to motor 62. If the resulting displacement is substantially equal to the desired predisplacement, then the slope of the corresponding force versus time curve is measured. Once the slope falls below predetermined level, the motor's maximum force is applied and the resulting displacement is monitored. If the resulting displacement being applied to the testing tip is substantially equal to the desired displacement, then the slope of the force versus time curve is determined such that once the slope is less than a predetermined level, data acquisition is discontinued and all data is stored within computer 76. Similar to creep deformation data, stress relaxation data can be saved and used immediately or at a later time.

FIG. 11 illustrates the steps used in measuring the thickness of articular cartilage 18. Generally, a maximum input force is applied via motor 62 to needle 88. As the needle translates, the resulting force measured by force transducer 70 is monitored by detector 64. Once the measured applied force becomes greater than the maximum desired force, then data acquisition will be discontinued and all data can be saved. Similar to creep deformation and stress relaxation measurements, thickness measurements utilize closed-loop control of force and displacement using the programmable arthroscopic evaluator of the present invention. However, instead of using a testing tip, as is used in creep deformation and stress relaxation measurements, thickness measurements require a small diameter needle 88 to be substituted for the larger diameter testing tip.

Figure 12:
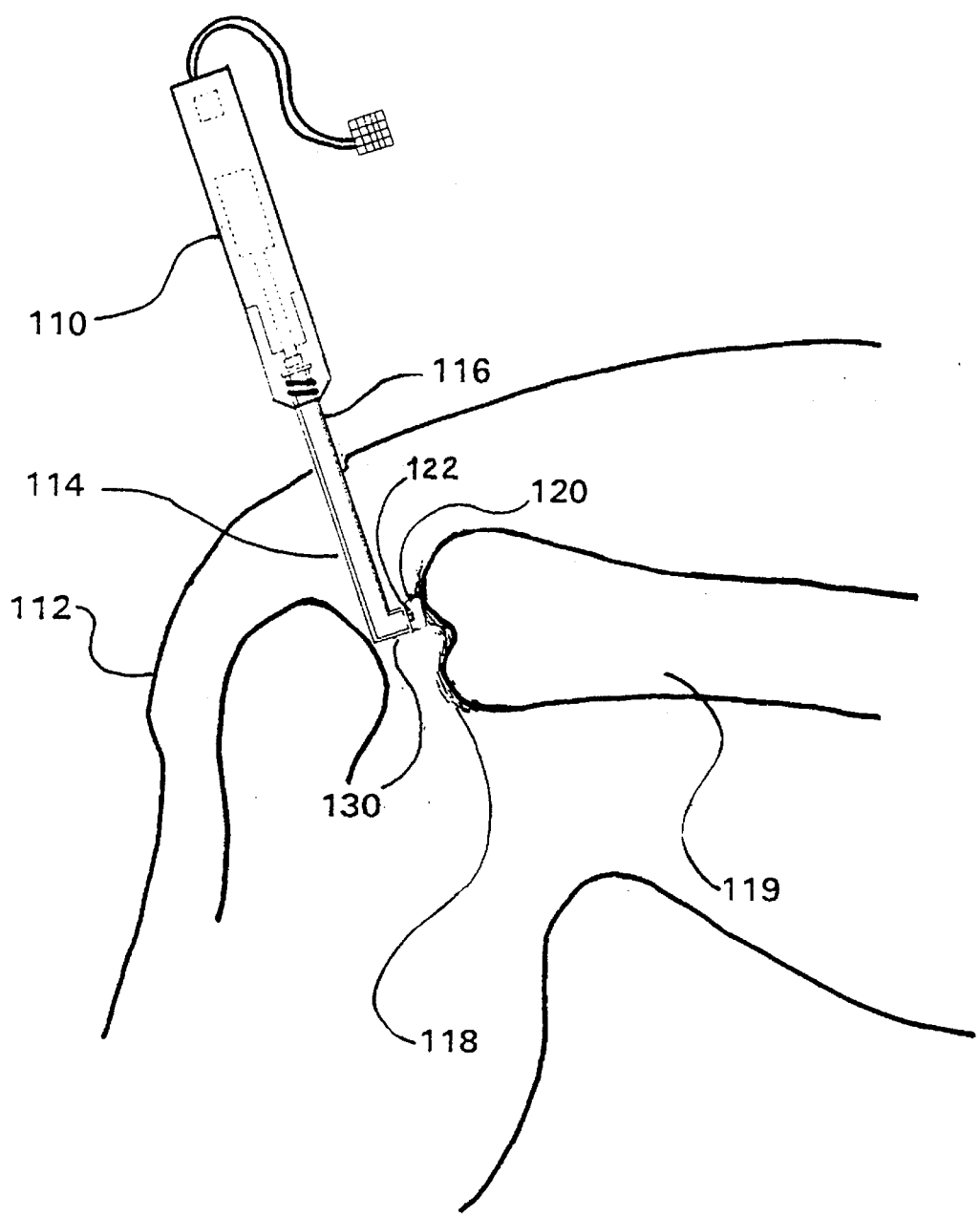
FIG. 12 depicts a miniaturized embodiment of the invention, the arthroscopic cartilage evaluator (ACE), showing the device as used to measure properties of articular cartilage of the knee, showing the size of the ACE relative to the knee.

An improved embodiment of the invention, comprising a hand-held testing component, called the arthroscopic cartilage evaluator (ACE) 110, is shown in FIG. 12. The hand-held portion of the ACE is preferably of a generally cylindrical shape. The distal end or head of the component is shown penetrating a patient's knee 112 through a small surgical incision 116, preferably about a 5 mm incision, into the joint cavity 114. The ACE comprises an alignment system to ensure that the force by the ACE against the articular cartilage is exerted perpendicularly. This alignment system includes perpendicularity rim 120 on the distal end of the ACE in contact with the articular cartilage 118 overlying the tip of the femur 119. The term distal is used with respect to the operator of the ACE, the handle being the proximal end and the end farthest from the operator being the distal end. After placement of the perpendicularity rim against the articular cartilage, testing tip 122 is moved to indent articular cartilage 118.

Figure 13:
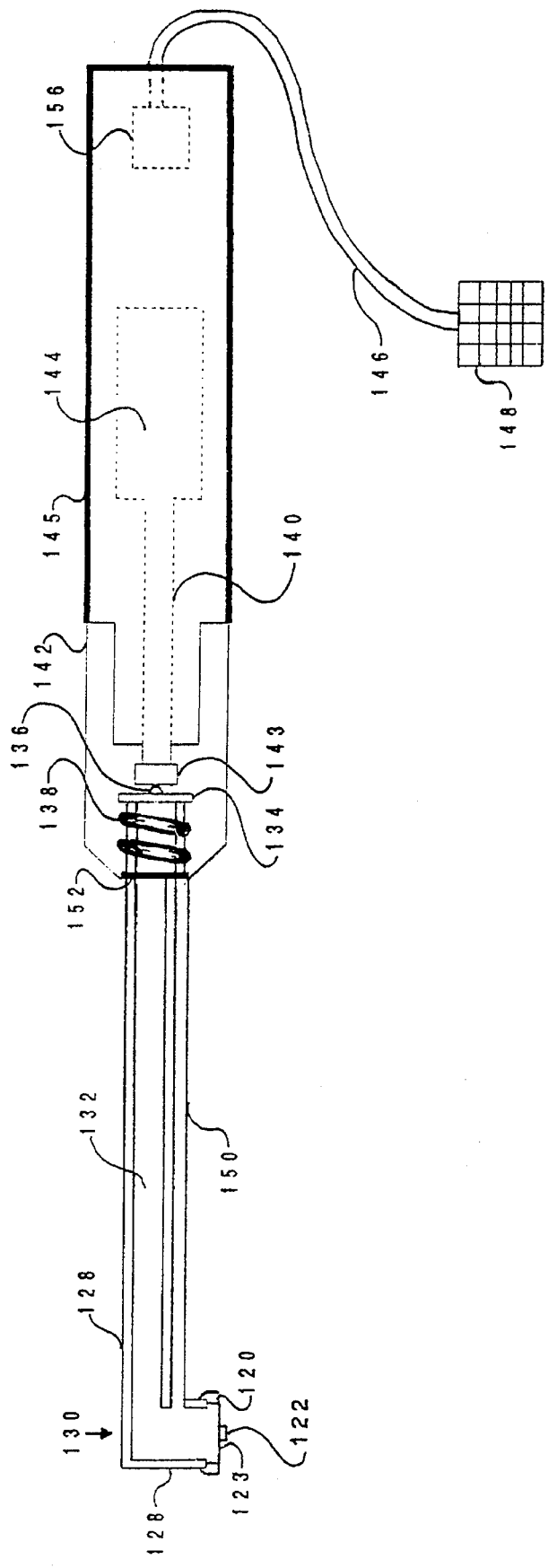
FIG. 13 depicts the hand-held component of the ACE in further detail.

FIG. 13 provides further details of the structure of the ACE. An electromechanical linear actuator, e.g. motor 144, preferably a DC encoder Mike Drive Model No. 18224, of Oriel Company, Stratford, Conn. having a maximum 22 pound force output and a resolution of 0.1 μm, in the handle of the ACE (the larger, proximal end of the device) is connected to motor shaft 140, the enlarged head of which rests against bearing 136, which is preferably a steel ball bearing, attached to the tip of linearly (axially) moving shaft 132. A contact-retaining spring 138 lies around linearly moving shaft 132 between fixed spring retainer 152 and movable spring retainer 134. Motor coupler 142 surrounds movable spring retainer 134 and is fixedly attached to the casing 145 of motor 144. Linearly moving shaft 132 is surrounded by sheath 128 which abuts fixed spring retainer 152. Sheath 128 may form an angle from about 30° to about 180° between its distal and proximal ends. The distal end of sheath 128 encloses head 130 and is preferably cylindrical in shape. Attached to the distal end of the head is perpendicularity rim 120 which forms a part of replaceable tip assembly 123.

Figure 15:
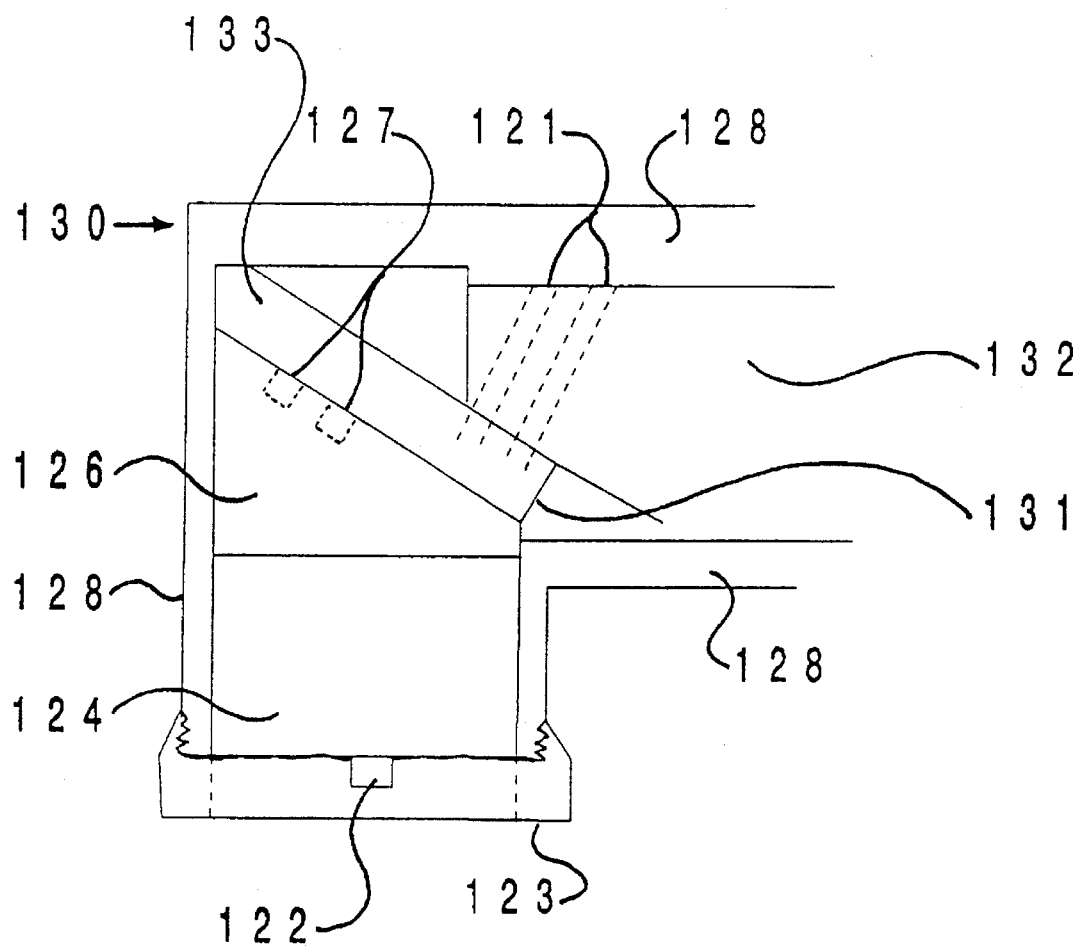
FIG. 15 depicts a side view of details of the head of the ACE.

The head is shown enlarged in FIG. 15. As shown in FIG. 15, linearly moving shaft 132 terminates at its distal end in a slider 131, which is connected to the distal end of linearly moving shaft 132, preferably using screws in slider screw holes 121. The underside of the distal end of shaft 132 slopes upward in the distal direction, preferably at an angle of about 30° for a head at a 90° angle from the handle. The slider 131 slidably engages with slide 133. Slide 133 abuts loading wedge 126. Force transducer 124, preferably force transducer 124 Model ALD-SP-MICRO of A.L. Design, Buffalo, N.Y., is operatively connected, preferably glued, to loading wedge 126. Testing tip 122 is part of the replaceable tip assembly 123. The testing tip 122 is operatively connected to force transducer 124, preferably by means of screwing replaceable tip assembly 123 to the threaded distal end of the sheath 128 surrounding the head of ACE. The entire assembly, comprising slider 131, slide 133, loading wedge 126, force transducer 124, and testing tip 122, is encased in sheath 128 which is preferably of stainless steel. As the device operates to indent the cartilage, shaft 132 moves forward, slider 131 forces the slide 133 to move downward. Slide 133 in turn, forces the loading wedge 126 to move downward, which in turn forces the force transducer 124, to move downward and which in turn forces testing tip 122 to move downward. As the device operates to retract the testing tip 122 from the cartilage, shaft 132 moves backward, and slider 131 forces the slide 133 to move upward. Slide 133 in turn pulls loading wedge 126 upward which pulls force transducer 124 and attached testing tip 122 upward away from the cartilage.

In the embodiment depicted herein the head 130 is at an angular orientation of 90° with respect to the handle but this angle may vary from about 30° to about 180°. The head may be replaceable so that different heads of different orientations may be attached to the handle, or the angle of the head may be adjustable.

Figure 16:
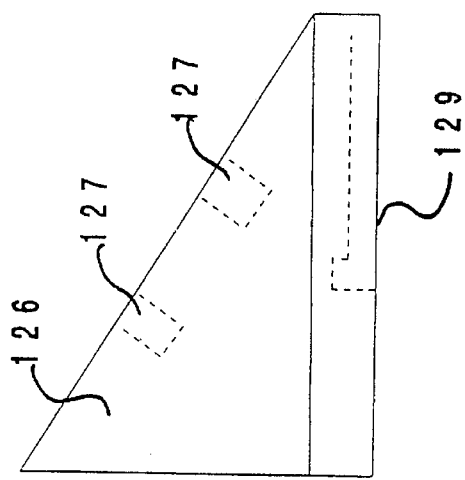
FIG. 16 is an enlarged side view of the loading wedge.

FIG. 16 is a side view of the loading wedge 126 showing wedge screw holes 127 and machine groove 129 for the force transducer excitation and signal wires. Preferably the loading wedge 126 has four symmetrical screw holes 127 and is attached to slide 133 using four screws. The acute angle of loading wedge 126 is preferably about 30° for a 90° head.

Figure 17:
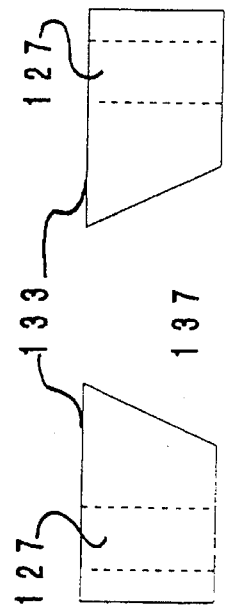
FIG. 17 is an enlarged three-dimensional view of the slider.
Figure 19:
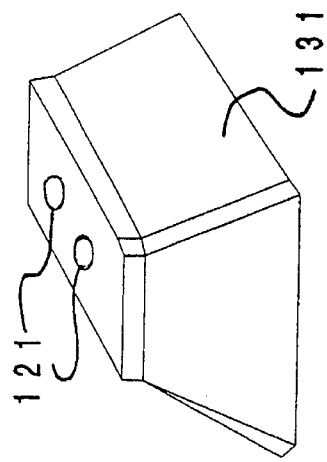
FIG. 19 is a front view of both halves of the slide.
Figure 18:
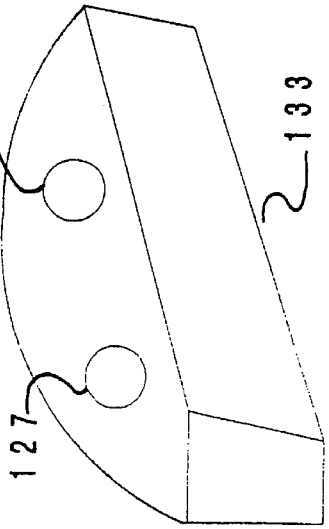
FIG. 18 is an enlarged three-dimensional view of one-half of the slide.
Figure 20:
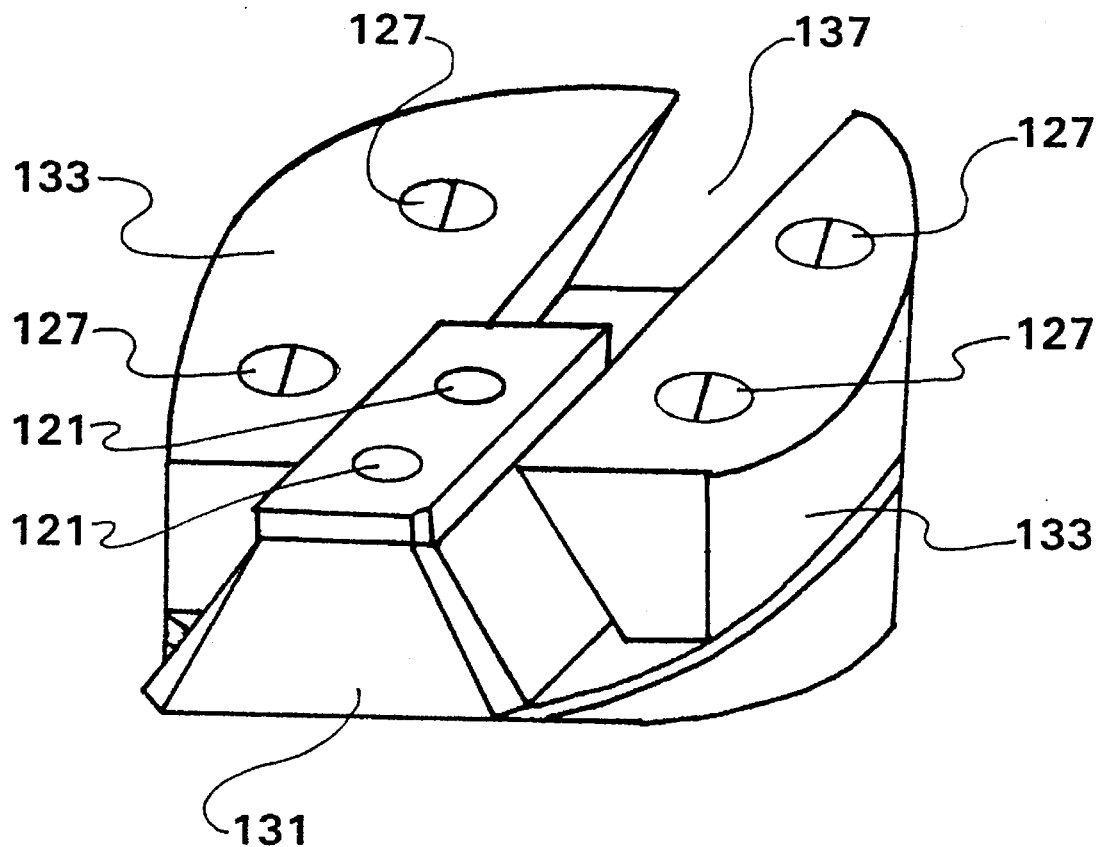
FIG. 20 is a three-dimensional view of the slide engaged with the slider.

FIG. 17 is a three-dimensional view of slider 131 showing slider screw holes 121, which are an extension of the slider screw holes 121 shown in FIG. 15, and adapted to receive screws connecting slider 131 to the distal end of shaft 132. Slider 131 is preferably shaped like a truncated tetrahedron. Slide 133, one-half of which is shown in three dimensions in FIG. 18, is connected to loading wedge 126 by screws extending into wedge screw holes 127 which extend into wedge 126 as shown in FIG. 16. FIG. 19 shows both halves of slide 133 from a viewpoint at the front end of the ACE looking downwardly in the direction of the long axis of slide 133. The two halves of slide 133 are attached to loading wedge 126 using screws extending into wedge screwholes 127 so as to form a slide channel 137 adapted to receive slider 131. FIG. 20 shows slider 131 engaged with slider 133 such that slider 131 is able to move in groove 137 between the two halves of slider 133.

Figure 21:
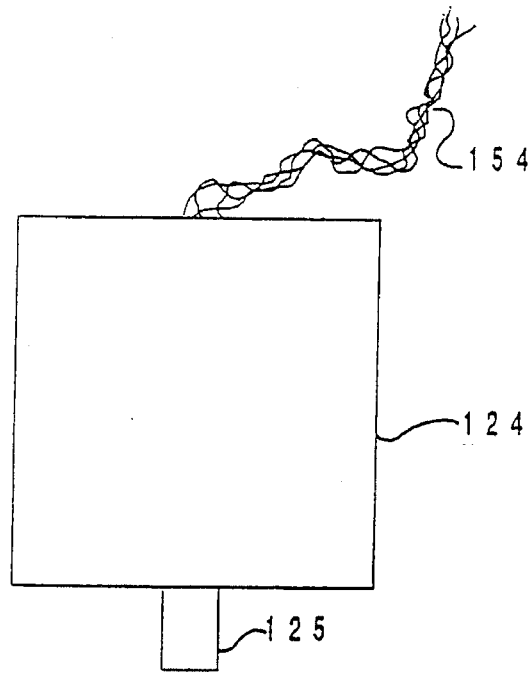
FIG. 21 is an enlarged side view of the force transducer.

FIG. 21 is an enlarged view of force transducer 124 showing force transducer excitation and signal wires 154 (which lead to fast connector 148 shown in FIG. 13) and force transducer probe 125.

Figure 22:
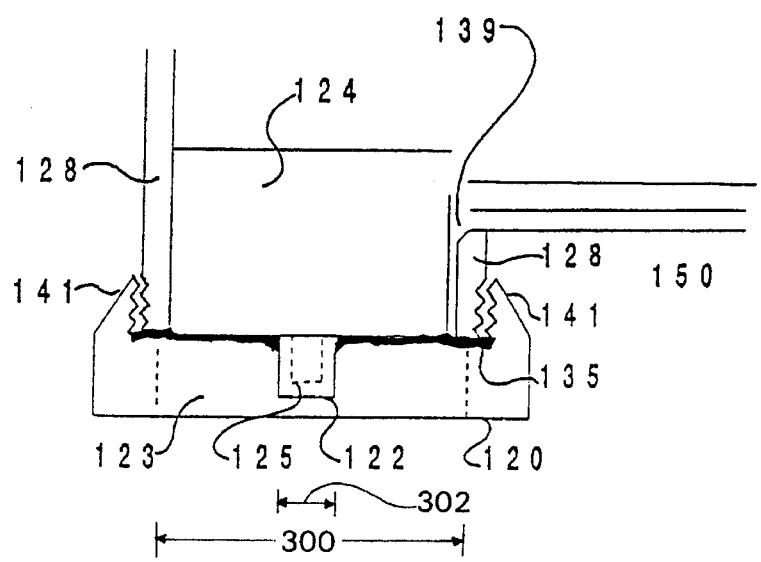
FIG. 22 is an enlarged side view of the distal portion of the head equipped with a replaceable tip assembly.

FIG. 22 depicts the distal portion of the ACE including replaceable tip assembly 123 comprising perpendicularity rim 120, having screw-threaded lips 141 adapted to screw onto the threaded distal end of sheath 128, and membrane 135, preferably a silicone rubber or latex membrane, attached e.g. by gluing to the proximal end of perpendicularity rim 120. Testing tip 122 has a recess into which force transducer probe 125 fits. The bottom, or distal surface of replaceable tip assembly 123 is a circle having an open center formed by perpendicularity rim 120. The bottom surface of perpendicularity rim 120 may be smooth or knurled. Also shown in FIG. 22 is pocket 139 for force transducer excitation and signal wires (not shown) formed in the end of transducer excitation and signal wire tube 150 which runs along the bottom of the proximal (or horizontal) portion of sheath 128. Sheath 128 is perforated and indented to accommodate pocket 139 and transducer excitation and signal wire tube 150. The force transducer excitation and signal wires lead from force transducer 124 to pocket 139, into transducer excitation and signal wire tube 150.

As shown in FIG. 13, the proximal end of the ACE is connected via data cable 146 to fast connector 148. Four force transducer excitation and signal wires 154 (best seen in FIG. 21) run from force transducer 124 along the underside of sheath 128 enclosed in transducer excitation and signal wire tube 150. These force transducer excitation and signal wires 154 run into the space inside motor coupler 142 and preferably through motor casing 145 to data cable 146, and thence to fast connector 148. Position detector data wires (not shown) from position detector 156, which is preferably an optical encoder built into the motor, also run into data cable 146. Data cable 146 contains a total of ten wires; four force transducer excitation and signal wires 154 (FIG. 21), three position detector data wires (not shown), and three motor controller wires (not shown).

Figure 14:
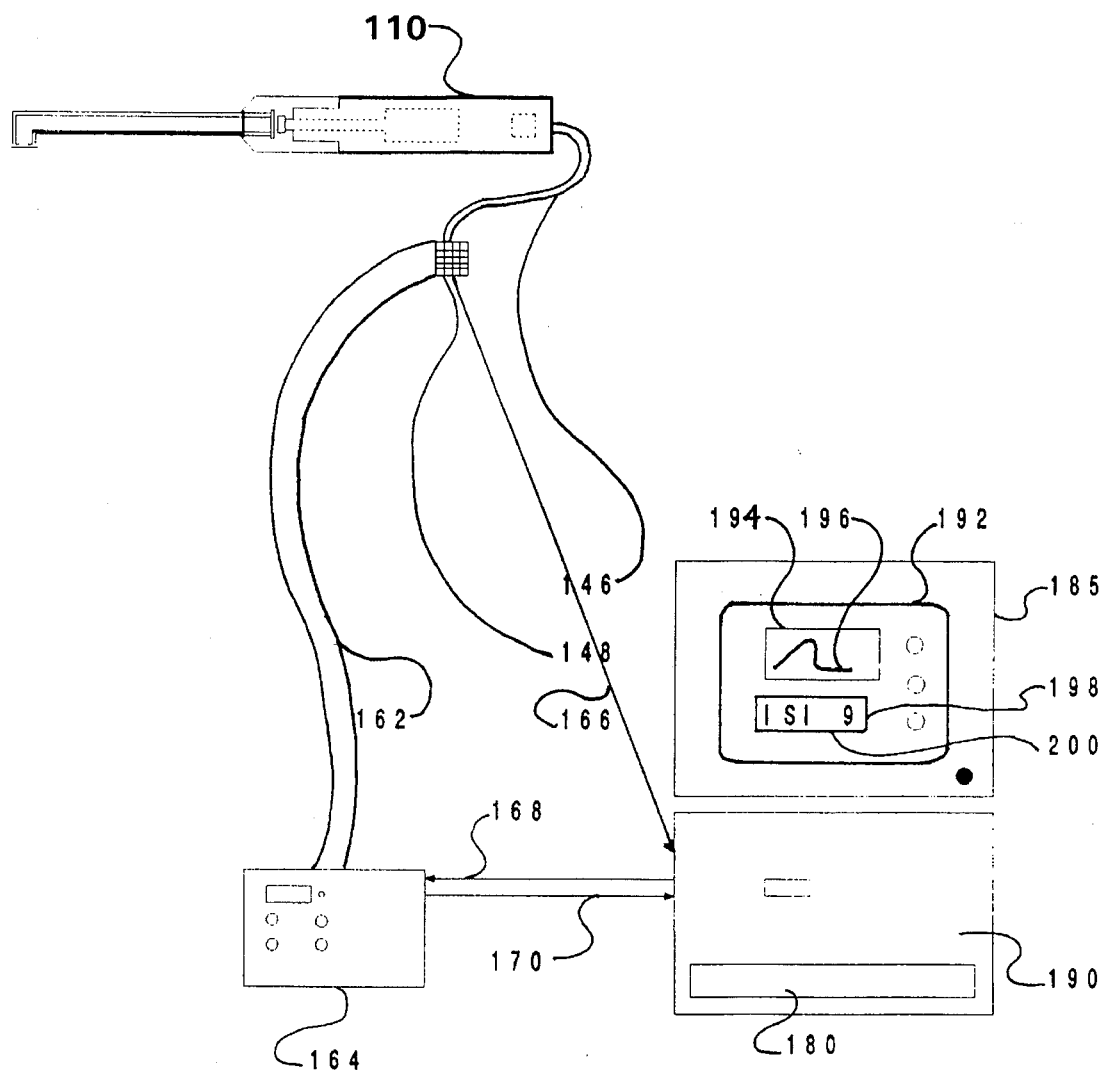
FIG. 14 is a diagram of the ACE in combination with its exterior control components showing the direction and flow of data collection and motor control signals and the resultant Index of Structural Integrity (ISI) display.

As shown in FIG. 14, the articular cartilage evaluator 110 is connected via data cable 146 to fast connector 148, which is connected via connector cable 162 to motor controller 164, preferably an Encoder Mike Control Station 18007 of Oriel Co., Stratford, Conn., which is in turn connected to computer 190 via displacement data line 170 (containing three wires) and motion control line 168 (containing three wires). Fast connector 148 is connected to computer 190 via force transducer data line 166. Computer 190 is preferably a Macintosh IIci with internal analog-to-digital and digital-to-analog and counter board 180, monitor 185, and screen 192. The output display consists of graph window 194 which displays a data graph 196 of displacement at a constant force over time or of force at a constant displacement over time, and index of structural integrity (ISI) window 198 in which appears the ISI display 200 preferably calculated from the data taken from measuring force data over time at a preset displacement of the articular cartilage.

In operation of the ACE 110, in a preferred embodiment, the head 130 of the ACE is inserted as shown in FIG. 12, into joint cavity 114 through small incision 116 in patient's knee 112. Then by translating or rotating the ACE 110, the head 130 is positioned perpendicularly to the articular surface of the cartilage 118 to be tested. This is easily accomplished by using the wide distal end equipped with perpendicularity rim 120 which is in contact with articular cartilage 118 and allows a large contact area between the distal end of head 130 and the articular cartilage. The entire test takes only a few seconds. Thus, there is no need to immobilize the instrument with an external positioning system. The perpendicularity rim 120 is pressed firmly against the surface of the articular cartilage by the operator and prevents movement of the ACE as a result of the resistance of the articular cartilage against the testing tip. If external mechanical support is needed, a kinematic assembly which includes a flexible arm consisting of serial spherical joints and a slide system for vertical positioning can be used to immobilize the ACE with respect to the joint.

A computer-based closed-loop speed control system as shown in FIG. 14 controls the process of data acquisition and display. The motor controller 164 of FIG. 14 commands the motor 144 in the handle of the ACE, seen in FIG. 13. For example, with reference to FIG. 13, the motor 144 moves the motor shaft 140 distally forward, at a constant speed of 189 μm per second (which corresponds to 100 μm per second movement of the testing tip 122), and computer-based data acquisition begins. This movement is translated to testing tip 122 which is preferably a 0.5 mm or less diameter, flat-ended, rigid, porous tip, by the following route: first the horizontal motion of the motor 144 is passed through motor shaft 140 by means of contact between the head of the motor shaft 143 and steel bearing 136 to linearly moving shaft 132. Contact retaining spring 138 is preloaded between fixed spring retainer 152 and movable spring retainer 134. This allows motor shaft 140 to always be in contact with steel bearing 136. The tapered ends of motor coupler 142 engaging the distal side of fixed spring retainer 152 cause compression of contact retaining spring 138 when linearly moving shaft 132 moves in the distal direction.

The motion of linearly moving shaft 132 is translated via slider 131 which is preferably attached to the distal end of shaft 132 using two screws (see FIG. 15) to slide 133 by a preset ratio, preferably 1.89:1 (i.e., when the linearly moving shaft 132 moves 1.89 μm horizontally, slide 133 moves 1 μm vertically). As will be appreciated by those skilled in the art, this ratio can be varied by varying the slope of the top of loading wedge 126. The slide 133 is preferably attached to loading wedge 126 using two screws (see FIG. 18). Downward movement of the slide thus causes corresponding downward movement of loading wedge 126. Details of the distal or head end of the ACE are shown in FIGS. 15, 22, 23 and 24. Since the force transducer 124 abuts loading wedge 126, the former also displaces vertically by the same amount, causing force transducer probe 125 to push against testing tip 122, which moves vertically downward against and into the articular cartilage.

Figure 23:
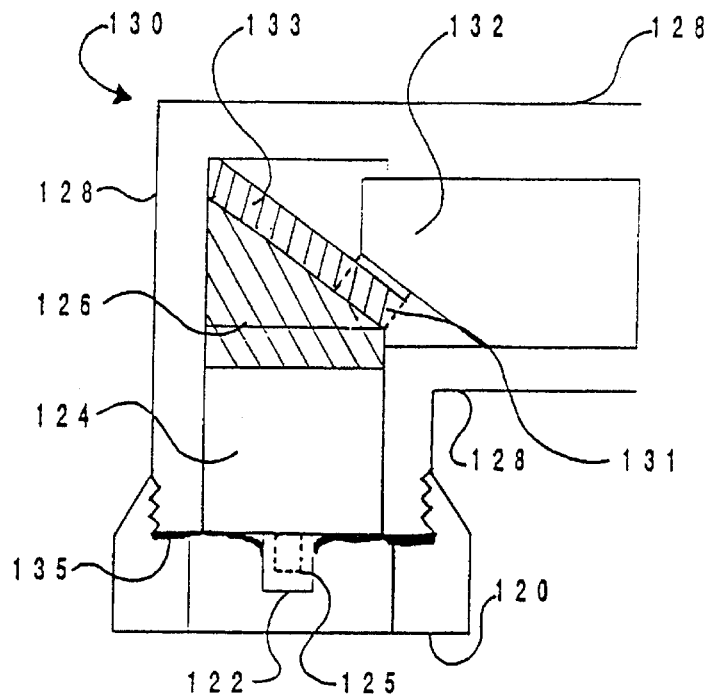
FIG. 23 is an enlarged side view of the head with the testing tip in the inactivated or fully retracted position.
Figure 24:
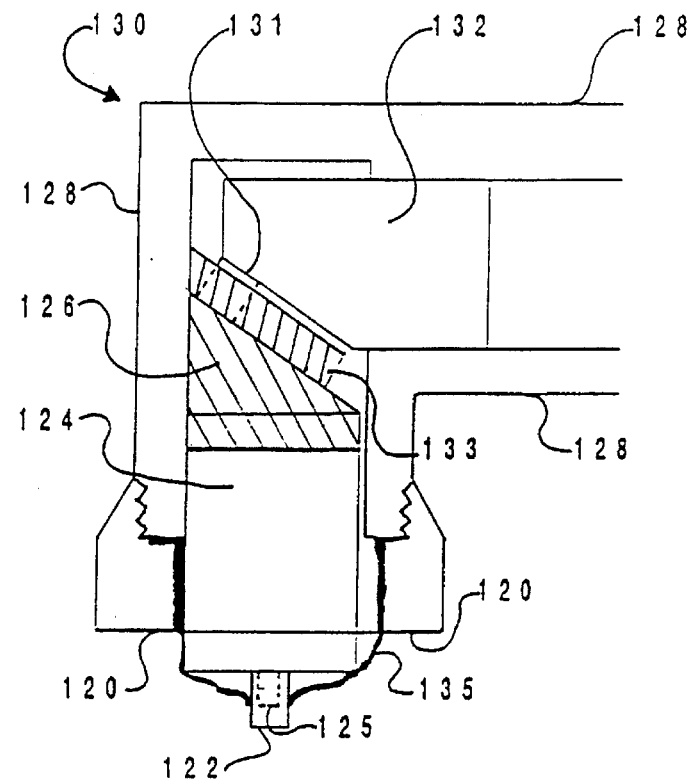
FIG. 24 is an enlarged side view of the head with the testing tip in the activated or fully extended position.

FIG. 23 shows the head 130 of the ACE with testing tip 122 in the "up" or inactivated position, and FIG. 24 shows the head 130 of the ACE with testing tip 122 in the "down" or activated position. (FIG. 24 shows a maximum activated position for the ACE. In practice when perpendicularity rim 120 rests against articular cartilage, the bottom surface of force transducer 124 will not extend beyond perpendicularity rim 120 unless the cartilage surface is substantially concave). Movement in the distal direction by linearly moving shaft 132 causes slider 131 which is fixedly attached to the underside of linearly moving shaft 132 and engaged with slide 133, to slide from the position shown in FIG. 23 along the length of slide 133 to the position shown in FIG. 24. Loading wedge 126 is pushed downward by the movement of slider 131, translating its motion to force transducer 124 and to force transducer probe 125 which pushes against testing tip 122, causing it to move through perpendicularity rim 120 and to push into and indent the articular cartilage.

As loading wedge 126 pushes against force transducer 124, the latter is activated to produce an electrical signal proportionate to the force applied against the articular cartilage 118 by testing tip 122. The output and input signals of the force transducer 124 are brought via force transducer excitation and signal wires 154 (best seen in FIG. 21) along the underside of sheath 128 (best seen in FIG. 22) enclosed in transducer excitation and signal wire tube 150 into the space inside motor coupler 142 (best seen in FIG. 13) and preferably through the casing 145 for motor 144 to data cable 146 and thence to fast connector 148. Input and output signals from the motor 144 are also sent via data cable 146 to fast connector 148. Input and output signals from the position detector 156 are transferred via position detector data wires (not shown) to data cable 146, and thence to fast connector 148.

When initiating testing, the operator sets the computer to indicate which portion of the body is being tested. As seen in FIG. 14, the force data read from the force transducer 124 are transmitted via force transducer data line 166 from the fast connector 148 to the computer 190. The data for data graph 196 start automatically being collected when the force becomes larger than a predetermined amount, preferably $9.8 \times 10^{-3}$N. The articular cartilage deformation is monitored with the position detector (encoder) 156 (seen in FIG. 13), preferably having a 0.1 μm resolution. Its output is collected and sent to computer board 180 via position detector data wires carried by data cable 146, fast connector 148, connector cables 162, motor controller 164, and displacement data line 170. The motor keeps moving at the above speed until the articular cartilage displacement reaches a preset value, preferably 10 μm. Data points are collected and plotted on data graph 196 displayed on graph window 194 of screen 192 of monitor 185.

Using the data collected and displayed as data graph 196, a computer algorithm is used to obtain the Index of Structural Integrity (ISI) resulting in ISI display 200. The ISI is a number from one to ten which can be used by the orthopaedist to evaluate the state of health or disease of the articular cartilage. The programs for controlling the ACE, generating the data graph 196 and the ISI display 200 are preferably written in LabView object oriented language (National Instruments, 6504 Bridge Point Parkway, Austin, Tex. 78730), and run on a Macintosh II ci (8 MB RAM).

Figure 25:
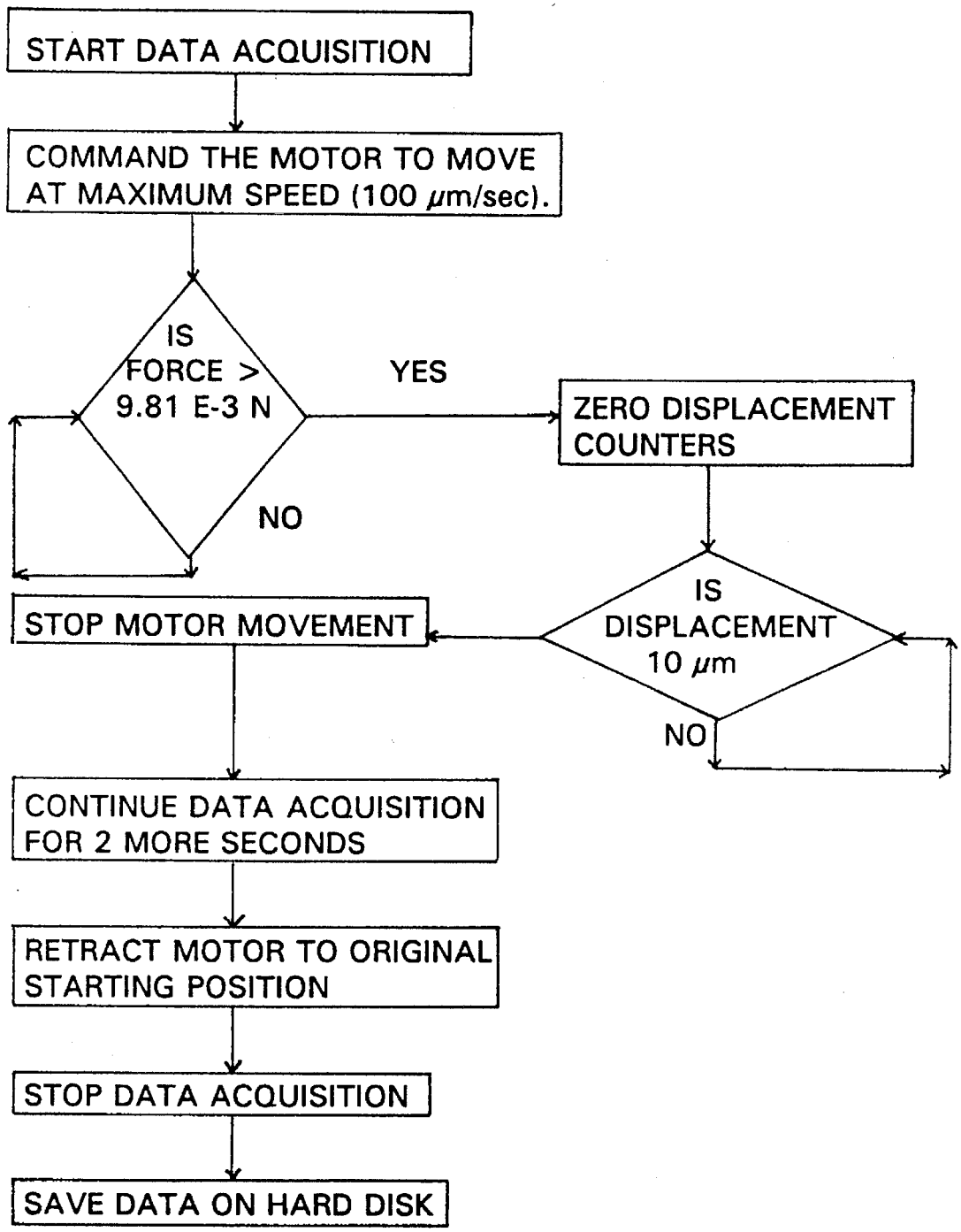
FIG. 25 is a flow diagram of steps used to perform the measurements and control the ACE of this invention as required to calculate the ISI.
Figure 26:
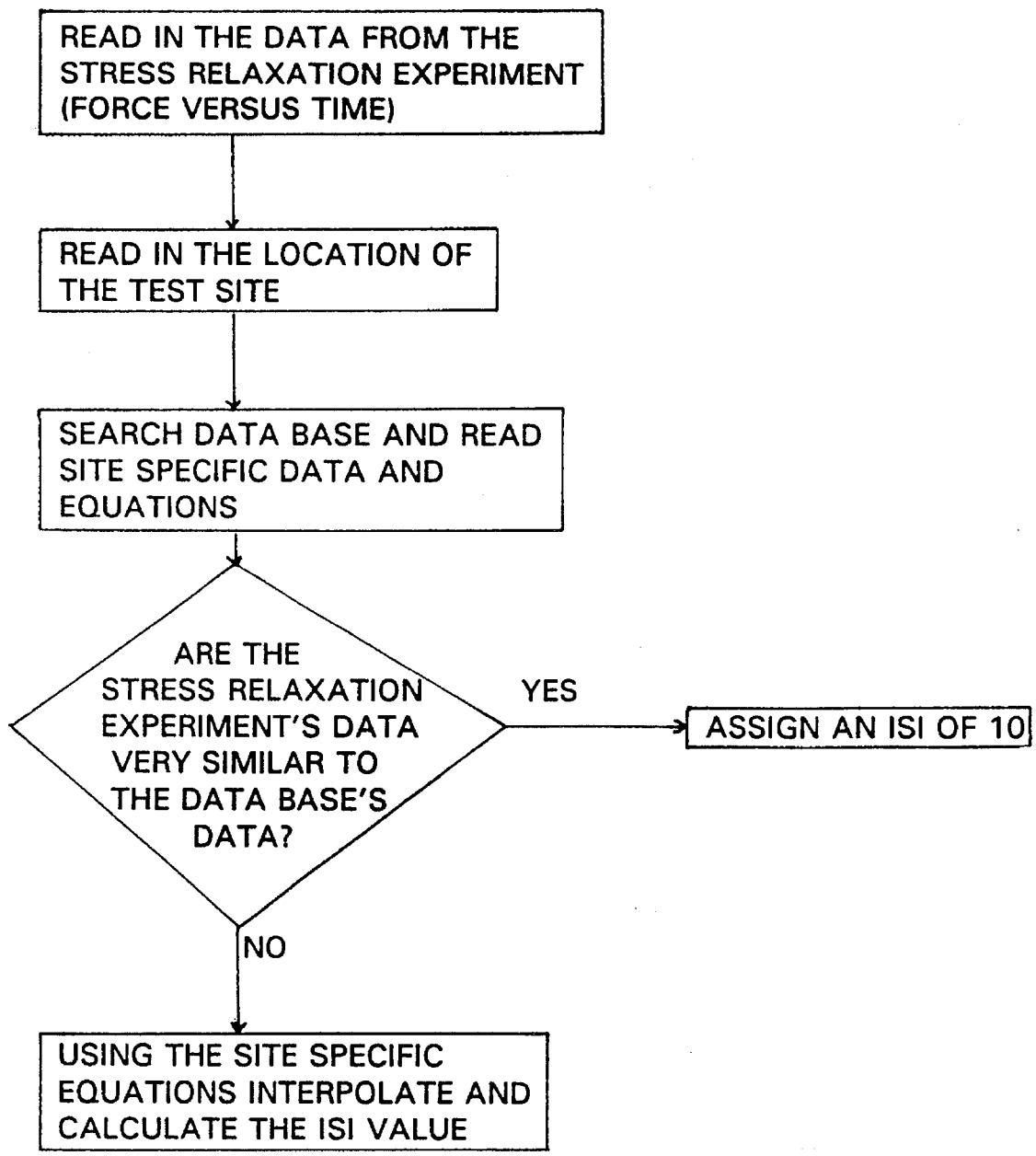
FIG. 26 is a flow diagram of steps used to measure and display the Index of Structural Integrity (ISI).

The algorithm used to control the ACE during data acquisition is shown in FIG. 25. The algorithm used to generate the ISI display using stress relaxation is shown in FIG. 26. The ISI is calculated after taking into consideration site specific data from a data base. Site specific data means data taken from tissue of the same type, i.e. from the same location in the body as that being tested. The method for generating the ISI comprises the steps of:

(a) indenting the cartilage to a predetermined displacement using a testing tip, and measuring the force required to achieve said displacement, preferably over time;

(b) determining, preferably using a computer, the ratio of said force or force versus time measurement to at least one corresponding measurement of tissue of the same type and of a known state of health, preferably healthy tissue. The measurement for the tissue having a known state of health may be a mean of a number of different measurements, preferably at least about twelve. The measurement for the healthy tissue is preferably assigned a numerical value of ten (the ISI).

(c) displaying said ratio as an integer from one to ten.

The measurements used to calculate the ISI may be stress relaxation data or creep deformation data, peak force required to achieve a predetermined indentation, area under the curve of a stress relaxation graph (preferably over a three second period), or most preferably peak force required to achieve a predetermined indentation multiplied by the amount of time required to reach this peak.

In a preferred embodiment, a database accumulated of the same data for healthy tissue taken from various locations in the body allows the measurements of the tissue being tested to be compared with healthy tissue of the same type. The operator sets the computer for the location in the body of the tissue being tested so that the test data will be compared with measurements for normal tissue of the same type.

At the end of a preset period, preferably one second, the computer 190 sends a binary signal to the motor controller (indexer) 164 which commands the motor to move at a constant speed, preferably 189 μm/sec (which corresponds to 100 μm per second movement of the testing tip 122), but this time in the opposite direction (away from the tissue). Linearly moving shaft 132 then moves toward motor 144, causing slider 131, sliding in the proximal direction on slide 133 to pull loading wedge 126, force transducer 124 and force transducer probe 125 upward whereby contact is maintained between bearing 136 attached to linearly moving shaft 132 and motor shaft 140. Testing tip 122 then retracts because it is attached to force transducer probe 125.

The ACE can then be removed from the joint cavity 114 and appropriate therapeutic measures taken based on the ISI reading displayed.

The entire mechanical test takes about three seconds. Preferably, the data collected are stress relaxation data, i.e. measurement of force exerted by the articular cartilage over time preferably under a step displacement, although as will be appreciated by those skilled in the art, the device may be as readily used to generate the ISI display using creep deformation data, i.e. measurement of articular cartilage displacement over time preferably under a step force.

The algorithm may be readily modified by using the creep deformation data instead of the stress relaxation data to generate the ISI display using creep deformation data.

In a preferred embodiment, the ACE is sensitive enough to apply and measure forces and displacements such that the thickness of the articular cartilage exerts a negligible effect (preferably less than about 0.10 percent, and more preferably less than 0.05 percent) on the reaction of the articular cartilage to indentation. For example, as is known in the art, the reaction of articular cartilage to a substantially small strain is unaffected by the tissue's thickness. When indentations on the order of 10 μm are used, the thickness of the articular cartilage need not be measured because the total strain applied as a result of such a small deformation is minuscule (about 0.04 percent). As such, calculating the material properties of the tissue, such as apparent compressibility (Poisson's ratio) compressire stiffness (aggregate modulus) and permeability is not needed for generation of the ISI. In addition, in such case thickness measurement is not required for determining the ISI. However, material properties may also be calculated using the device of this invention. Thickness measurements are not required for such calculations and they can be approximated as long as the applied strain or stress is substantially small.

For the above reasons, in a preferred embodiment, the cartilage evaluator includes a loading system which is adapted to indent less than about 20, 30, or 50 microns during use, and preferably less than about 10 microns during use. In general, less cartilage indentation results in less damage or harm (whether real or potential) to the cartilage.

In a preferred embodiment the cartilage evaluator is adapted to measure the response of cartilage in less than about 10, 20, or 30 seconds, and more preferably less than about 3 or 5 seconds, during use. In such circumstances, the practitioner can quickly move the evaluator over different portions of the cartilage, rapidly stopping to obtain "spot"

evaluations of the response and material properties of the cartilage during use.

Significantly, the cartilage evaluator of preferred embodiments of this invention may be adapted to evaluate the cartilage during use without harming to any portion of the cartilage. As such, the nondestructive nature of this evaluator enables the practitioner to use the evaluator to widely, carefully, and unsparingly scan different portions of cartilage without fear of doing more harm by testing than would have resulted if no testing was conducted.

As shown in FIG. 22, in a preferred mode the inside diameter 300 of the perpendicularity rim 120 is at least 5–10 times the diameter 302 of testing tip 122. In this manner, strain and other surface factors created when the cartilage contacts the edges of perpendicularity rim 120 are inhibited from propagating and/or affecting cartilage that contacts the testing tip 122.

The foregoing description of the present invention has therefore been directed to particular preferred embodiments. It will be apparent, however, to those skilled in the art that modifications and changes in the various devices and methods described above may be made without departing from the scope and spirit of the invention. For example, any computer-based, closed-loop feedback system incorporating a motor, a positional detector, with or without a force transducer, may be made without departing from the scope and spirit of the invention regardless of how the various components are arranged or coupled to each other provided the resulting measurements are acquired using an automatic computer-based system. Therefore, equivalent elements may be substituted for those illustrated and described herein. Parts may be reversed, and certain features of the invention may be utilized independently of the use of other features, all as would be apparent to one skilled in the art after having benefitted from the description of the invention. As can be appreciated from the above discussion, the invention can present a practical advance over conventional manual indenter devices which, by their nature, cannot achieve the level of accuracy obtained from the computer-based closed-loop system of the present invention. Similarly, the present invention represents an advance in the art of cartilage evaluation in that it provides and displays, in the Index of Structural Integrity, a single number from one to ten which enables the physician to quickly, objectively and repeatably measure the health of a patient's cartilage tissue in vivo in his office.

What is claimed is:

1. A device for measuring the response of cartilage to indentation in vivo comprising:

a hand-held component insertable through an incision to a position proximate the cartilage, said component comprising a loading system and an alignment system, said loading system comprising a testing tip for indenting the cartilage during use, and a means for moving the testing tip relative to the alignment system a set displacement to cause a predetermined amount of indentation into the cartilage, said alignment system adapted to align the testing tip substantially perpendicular to the surface of cartilage during use; and a response system for measuring the force versus time response of the cartilage to said set displacement and indentation during use.

2. The device of claim 1 wherein said loading system also comprises means for applying a predetermined continuous force to the testing tip to cause displacement of the testing tip relative to the alignment system and indentation of the testing tip into the cartilage; and a response system for measuring the displacement versus time response of the cartilage to said predetermined force causing said indentation during use.

3. The device of claim 2 wherein said loading system also comprises means for applying said predetermined force to said testing tip at a known rate.

4. The device of claim 2 comprising (a) an electromechanical actuator comprising a motor adapted to move the testing tip to apply a force over time to the cartilage during use whereby the cartilage can be indented by the testing tip during use;

(b) a force transducer adapted to measure the force applied to the cartilage by the testing tip during use;

(c) a position detector adapted to measure over time the position of the loading system and resultant displacement of the cartilage by the testing tip during use; and (d) a computer operatively connected to the actuator, force transducer and position detector during use, whereby the computer is adapted to control the actuator over time during use.

5. The device of claim 4 wherein the position detector comprises a linear variable differential transformer having an infinite displacement resolution.

6. The device of claim 1, further comprising a computer adapted to calculate stress relaxation of the cartilage during use as a function of measured force exerted upon the cartilage by the testing tip over time at a set displacement.

7. The device of claim 1, further comprising a computer adapted to calculate the aggregate modulus, Poisson's ratio, or permeability of the cartilage.

8. The device of claim 1, further comprising a computer adapted to calculate the Index of Structural Integrity of the cartilage.

9. The device of claim 1 wherein the alignment system comprises a perpendicularity rim or non-circular perpendicularity flanges extending outward from the distal end of a sheath surrounding at least a portion of said loading system.

10. The device of claim 1 comprising:

(a) a computer adapted to establish and maintain a desired position for the testing tip during a data-acquisition period; and (b) during the data-acquisition period, a computer adapted to collect force versus time measurement data.

11. The device of claim 10 further comprising:

(a) a computer adapted to establish a desired position for the testing tip during a pre-data acquisition period; and (b) during the pre-data acquisition period, a computer adapted to collect force versus time measurement data for determining the point for beginning the data acquisition period.

12. The device of claim 1, further comprising:

(a) a computer system for determining the ratio of measured force required to achieve a preset cartilage displacement to at least one corresponding measurement for healthy tissue of the same type wherein said healthy tissue measurement is assigned a numerical value of ten; and (b) a system operatively connected to said computer system for determining said ratio and for displaying said ratio as an integer from one to ten.

13. The device of claim 1 wherein said loading system further comprises a force translation system connected to a motor shaft and said testing tip for changing the direction of the motion imparted to said testing tip by said motor shaft during use.

14. The device of claim 13 wherein said force translation system comprises a slider fixedly attached to said motor shaft, said slider being adapted to move at an angle to said motor shaft in response to force imparted by said motor shaft during use.

15. The device of claim 14 comprising a force transducer between the slider and the testing tip operatively connected to a computer whereby the force exerted by the cartilage against the testing tip is measured during use.

16. The device of claim 13 wherein said force translation system is adapted to change the speed of the motion of the motor shaft imparted to the testing tip during use.

17. The device of claim 1 comprising a position detector operatively connected to a computer and said loading system whereby the position of the testing tip with respect to the cartilage is measured and controlled during use.

18. The cartilage evaluator of claim 1 comprising a replaceable testing tip assembly comprising a perpendicularity rim and a testing tip.

19. The device of claim 1 wherein the loading system is adapted to indent less than about 50 microns during use.

20. The device of claim 1 wherein the loading system is adapted to indent less than about 10 microns during use.

21. The device of claim 1 wherein the device is adapted to measure the response of cartilage in less than about 10 seconds during use.

22. The device of claim 1 wherein the device is adapted to measure the response of cartilage in less than about 5 seconds during use.

23. The device of claim 1 wherein the device is adapted to evaluate the cartilage during use without harming any portion of the cartilage.

24. The device of claim 1 adapted to evaluate the cartilage without determining the thickness of the cartilage.

25. The device of claim 1 wherein the testing tip has a diameter, and wherein the perpendicularity rim has an inside diameter which is at least about 5 times greater than the diameter of the testing tip.

26. The device of claim 1 adapted to evaluate articular cartilage of a human knee.

27. A device for measuring the response of cartilage to indentation in vivo, comprising:

a hand-held component insertable through an incision to a position proximate the cartilage, said component comprising a loading system and an alignment system, said loading system comprising a testing tip for indenting the cartilage during use, and means for applying a predetermined continuous force to the testing tip to cause displacement of the testing tip relative to the alignment system and indentation of the testing tip into the cartilage, said alignment system adapted to align the testing tip substantially perpendicular to the surface of cartilage during use; and a response system for measuring the displacement versus time response of the cartilage to said predetermined force causing said indentation during use.

28. The device of claim 27, further comprising a computer adapted to calculate creep deformation of the cartilage during use as a function of measured displacement of the cartilage over time as a function of a constant force exerted upon the cartilage.

29. The device of claim 27, further comprising a computer adapted to calculate the aggregate modulus, Poisson's ratio, or permeability of the cartilage.

30. The device of claim 27 wherein the alignment system comprises a perpendicularity rim or non-circular perpendicularity flanges extending outward from the distal end of a sheath surrounding at least a portion of said loading system.

31. The device of claim 27 comprising:

(a) a computer adapted to determine a zero position for the testing tip at the cartilage tissue surface;

(b) a computer adapted to establish and control the actuator to maintain a predetermined force against the cartilage by the testing tip during a data-acquisition period; and (c) during the data acquisition period, a computer adapted to collect cartilage displacement versus time measurement data.

32. The device of claim 27 wherein said loading system further comprises a force translation system connected to a motor shaft and said testing tip for changing the direction of the motion imparted to said testing tip by said motor shaft during use.

33. The device of claim 32 wherein said force translation system comprises a slider fixedly attached to said motor shaft, said slider being adapted to move at an angle to said motor shaft in response to force imparted by said motor shaft during use.

34. The device of claim 33 comprising a force transducer between the slider and the testing tip operatively connected to a computer whereby the force exerted by the cartilage against the testing tip is measured during use.

35. The device of claim 32 wherein said force translation system is adapted to change the speed of the motion of the motor shaft imparted to the testing tip during use.

36. The device of claim 27 comprising a force transducer operatively connected to a computer and said loading system whereby the force exerted by the testing tip against the cartilage is measured and controlled during use.

37. The cartilage evaluator of claim 27 comprising a replaceable testing tip assembly comprising a perpendicularity rim and a testing tip.

38. The device of claim 27 wherein the loading system is adapted to indent less than about 50 microns during use.

39. The device of claim 27 wherein the loading system is adapted to indent less than about 10 microns during use.

40. The device of claim 27 wherein the device is adapted to measure the response of cartilage in less than about 10 seconds during use.

41. The device of claim 27 wherein the device is adapted to measure the response of cartilage in less than about 5 seconds during use.

42. The device of claim 27 wherein the device is adapted to evaluate the cartilage during use without harming any portion of the cartilage.

43. The device of claim 27 adapted to evaluate the cartilage without determining the thickness of the cartilage.

44. The device of claim 27 wherein the testing tip has a diameter, and wherein the perpendicularity rim has an inside diameter which is at least about 5 times greater than the diameter of the testing tip.

45. The device of claim 27 adapted to evaluate articular cartilage of a human knee.

* * * * *